(12) United States Patent
Safonov et al.

(10) Patent No.: US 12,257,132 B2
(45) Date of Patent: Mar. 25, 2025

(54) HYDROGEN-DELIVERING SYSTEM FOR A BODILY ORIFICE

(71) Applicant: H2 Universe LLC, Granbury, TX (US)

(72) Inventors: Vladimir L. Safonov, Grandbury, TX (US); Christian S. Yorgure, Rochester, NY (US); Marina Yu Safonov, Granbury, TX (US)

(73) Assignee: H2 Universe LLC, Granbury, TX (US)

( * ) Notice: Subject to any disclaimer, the term of this patent is extended or adjusted under 35 U.S.C. 154(b) by 1045 days.

(21) Appl. No.: 17/140,631

(22) Filed: Jan. 4, 2021

(65) Prior Publication Data

US 2021/0220185 A1    Jul. 22, 2021

Related U.S. Application Data

(60) Provisional application No. 62/974,923, filed on Jan. 2, 2020.

(51) Int. Cl.
| | | |
|---|---|---|
| *A61K 33/00* | (2006.01) | |
| *A61F 13/20* | (2006.01) | |
| *A61F 13/34* | (2006.01) | |
| *A61F 13/551* | (2006.01) | |
| *A61M 31/00* | (2006.01) | |
| *A61F 13/15* | (2006.01) | |

(52) U.S. Cl.
CPC ...... *A61F 13/2074* (2013.01); *A61F 13/2051* (2013.01); *A61F 13/34* (2013.01); *A61F 13/55175* (2013.01); *A61K 33/00* (2013.01); *A61M 31/00* (2013.01); *A61F 2013/15097* (2013.01); *A61M 2202/02* (2013.01); *A61M 2210/1067* (2013.01)

(58) Field of Classification Search
CPC .. A61F 13/2074; A61F 13/2051; A61F 13/34; A61F 13/55175; A61F 2013/15097; A61K 33/00; A61M 2202/02; A61M 2210/1067; A61M 2210/1475; A61M 31/00
See application file for complete search history.

(56) References Cited

U.S. PATENT DOCUMENTS

| | | |
|---|---|---|
| 8,852,660 B2 | 10/2014 | Miljkovic |
| 10,076,540 B1 | 9/2018 | Perricone |
| 2003/0139709 A1* | 7/2003 | Gehling ............. A61F 13/2051 604/360 |
| 2007/0110676 A1 | 5/2007 | Clymer et al. |
| 2008/0161752 A1* | 7/2008 | Rajala .................. A61M 31/00 604/48 |
| 2009/0326447 A1* | 12/2009 | Joshi ..................... A61K 31/00 604/82 |

(Continued)

OTHER PUBLICATIONS

Amirkhani, et al., "Relation between Fluoxetine and Menstrual Cycle Disorders," Journal of Family and Reproductive Health, vol. 6, No. 3, pp. 95-98, 2012.

(Continued)

*Primary Examiner* — Nathan R Price
*Assistant Examiner* — Haden Matthew Ritchie
(74) *Attorney, Agent, or Firm* — Morgan, Lewis & Bockius LLP

(57) ABSTRACT

A system for delivery of molecular hydrogen ($H_2$) into a bodily orifice of a subject, such as the vagina or anus/rectum, to provide therapeutic effect.

20 Claims, 8 Drawing Sheets

(56) References Cited

U.S. PATENT DOCUMENTS

| | | |
|---|---|---|
| 2013/0034542 A1 | 2/2013 | Ganter et al. |
| 2013/0323190 A1 | 12/2013 | Ohta et al. |
| 2015/0258136 A1 | 9/2015 | Lucas |
| 2018/0092816 A1 | 4/2018 | Perricone et al. |
| 2019/0308001 A1 | 10/2019 | Safonov |
| 2020/0030372 A1 | 1/2020 | Safonov et al. |
| 2020/0345992 A1 | 11/2020 | Safonov et al. |

OTHER PUBLICATIONS

Dixon, et al., "The evolution of molecular hydrogen: a noteworthy potential therapy with clinical significance," Medical Gas Research, vol. 3, No. 10, 12 pages, 2013.

Harel, "Dysmenorrhea in Adolescents and Young Adults: Etiology and Management," J Pediatr Adolesc Gynecol, vol. 19, pp. 363-371, 2006.

Huang, et al., "Recent advances in hydrogen research as a therapeutic medical gas," Free Radical Research, 44(9): Sep. 2010, DD. 971-982.

Khodakarami, et al., "The Severity of Dysmenorrhea and its Relationship with Body Mass Index among Female Adolescents in Hamadan, Iran," Journal of Midwifery & Reproductive Health, vol. 3, No. 4, pp. 444-450, 2015.

Kobayashi, et al., "Hydrogen generation by reaction of Si nanopowder with neutral water," J Nanopart Res, vol. 19, 9 pages, 2017.

Screen shot of Krucik, G., Acute upper respiratory infection, 2013, https://www.healthline.com/health/ acute-upper-respiratory-infection#causes from The Wayback Machine (Year: 2013).

Matei, et al., "Emerging mechanisms and novel applications of hydrogen gas therapy," Medical Gas Research, vol. 8, No. 3, pp. 98-102, 2018.

Negriff, et al., "The measurement of menstrual symptoms: Factor structure of the menstrual symptom questionnaire in adolescent girls," J Health Psychol. vol. 14, No. 7, pp. 899-908, 2009.

Nicolson, et al., "Clinical Effects of Hydrogen Administration: From Animal and Human Diseases to Exercise Medicine," International Journal of Medicine, vol. 7, pp. 32-76, 2016.

Ohta, "Recent Progress Toward Hydrogen Medicine: Potential of Molecular Hydrogen for Preventive and Therapeutic ADDlications," Current Pharmaceutical Design, 17, 2011, DD. 2241-2252.

Ostojic, "Should hydrogen therapy be included in a musculoskeletal medicine routine?" F1000 Research, vol., 5 pages, 2016.

Safonov, et al., "Hydrogen nanobubbles in a water solution of dietary supplement," Colloids and Surfaces A: Physicochemistry Engineering Aspects, vol. 436 (2013), DD. 333-336.

Unsal, et al., "Evaluation of Dysmenorrhea Among Women and its Impact on Quality of Life in a Region of Western Turkey," Pak J Med Sci, vol. 26, No. 1, pp. 142-147, 2010.

Unsal, et al., "Prevalence of dysmenorrhea and its effect on quality of life among a group of female university students," Upsala Journal of Medical Sciences, vol. 115, No. 2, pp. 138-145, 2010.

Wang, et al., "The cytokine storm and factors determining the sequence and severity of organ dysfunction in multiple organ dysfunction syndrome," The American Journal of Emergency Medicine, vol. 26, pp. 711-715, 2008.

Wat, "The common cold: a review of the literature," European Journal of Internal Medicine, vol. 15, pp. 79-88, 2004.

Kanehira, et al. "Controllable hydrogen release via aluminum powder corrosion in calcium hydroxide solutions," J. Asian Ceramic Societies, vol. 1, 2013: pp. 296-303.

Shields, et al., "Still too hot: Examination of water temperature and water heater characteristics 24 years after manufacturers adopt voluntary temperature settings," Nat Rev Immunol, vol. 18, 2018: pp. 168-182.

\* cited by examiner

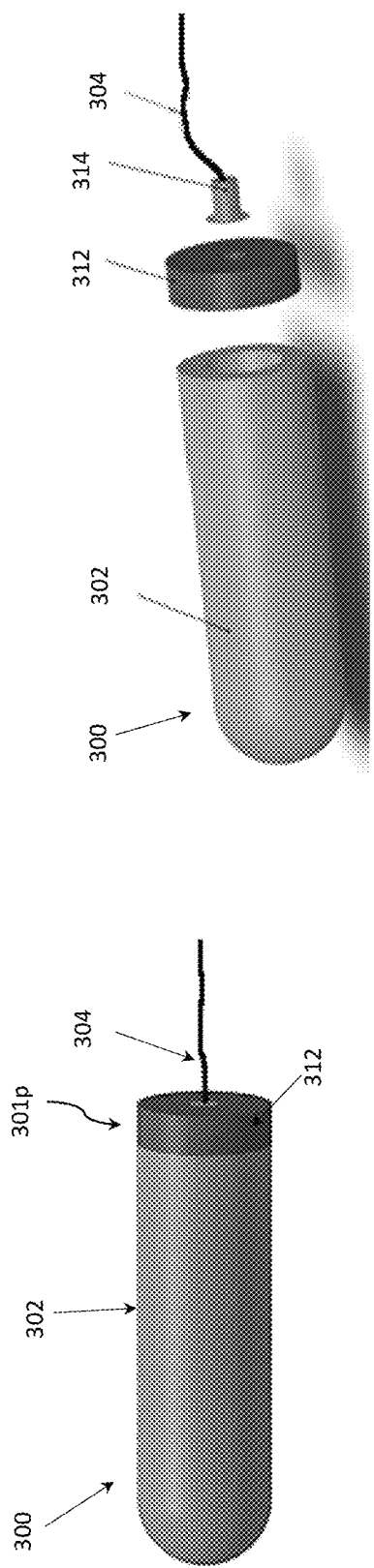
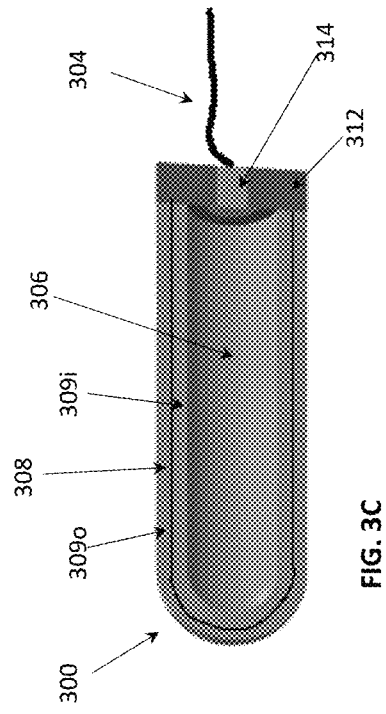
FIG. 3B
FIG. 3A
FIG. 3C

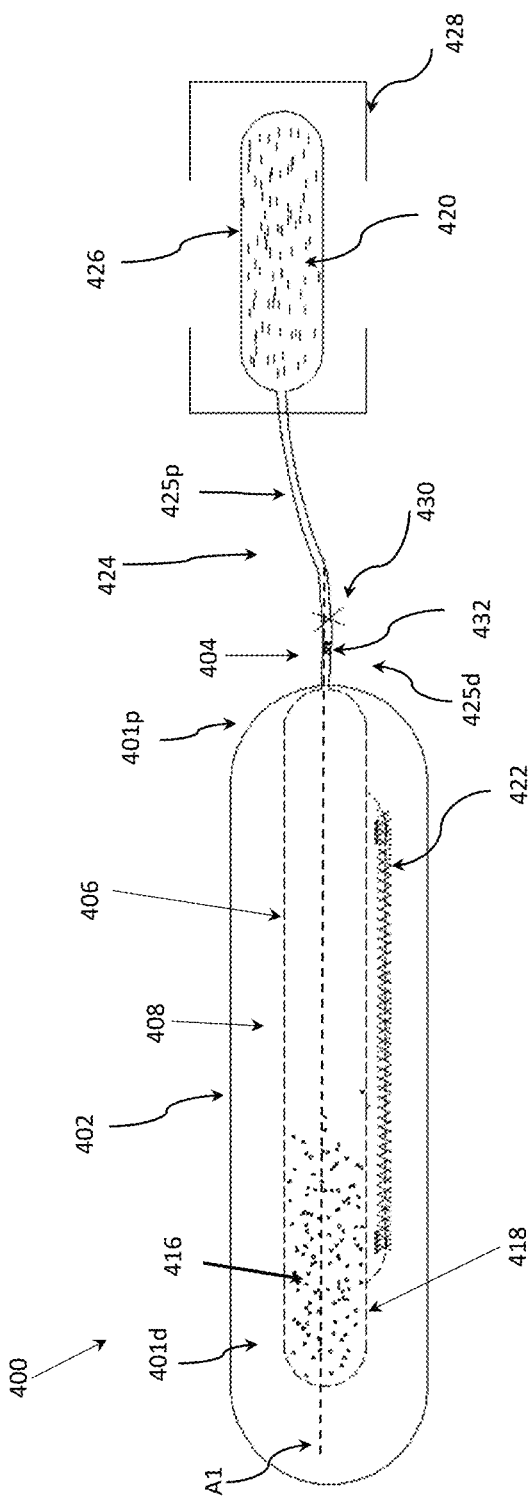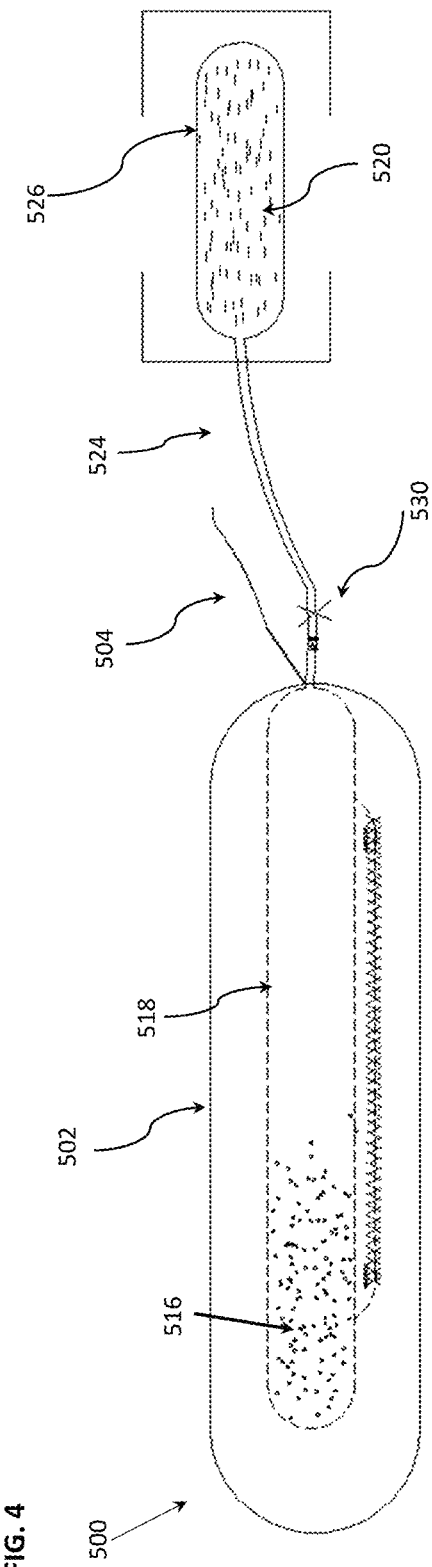
FIG. 4
FIG. 5

100 # HYDROGEN-DELIVERING SYSTEM FOR A BODILY ORIFICE

RELATED APPLICATIONS

This application claims priority to and benefit of U.S. Provisional Application No. 62/974,923 filed Jan. 2, 2020, the entire content of which is incorporated herein by reference.

TECHNICAL FIELD

The present disclosure relates to a hydrogen-delivering system for administration to a subject's bodily orifice, such as a vagina or anus/rectum, for delivery of molecular hydrogen thereby providing therapeutic effects.

BACKGROUND

Hydrogen therapy includes the use of molecular hydrogen ($H_2$) for treatment and prevention of various conditions and diseases. Basic and clinical research has revealed that hydrogen is an important physiological regulatory factor with antioxidant, anti-inflammatory, and anti-apoptotic protective effects on cells and organs. See Huang et al., *Free Radical Res.* (2010) 44(9): 971-82; Ohta, *Curr Pharm Des.* (2011) 17(22): 2241-52; Nicolson et al., *International Journal of Clinical Medicine*. (2016) 7:32-76; Matei et al., *Medical Gas Research*, 2018, vol. 8(3), pp. 98-102. Effects of the $H_2$ treatment were documented for many oxidative stress-related diseases, and hydrogen-based therapy is a rapidly growing area.

Existing methods for delivering of hydrogen to a subject's body include administration of $H_2$ inhalations, oral administration of hydrogen-infused liquids (e.g., $H_2$-enriched water) or hydrogen-releasing solids (e.g., capsules or tablets), injecting $H_2$-containing solutions (e.g., $H_2$-infused saline, delivered intravenously), bathing in hydrogen-enriched water, and other ways of delivering hydrogen to the subject's body. These methods have their advantages and disadvantages and serve certain purposes of prevention, healing, and therapy.

There remains a need for systems and methods that make use of therapeutic properties of molecular hydrogen.

SUMMARY

In embodiments, hydrogen-delivering systems, devices, and methods of using the same are provided that allow administering molecular hydrogen ($H_2$) to tissues in a bodily orifice of a subject. The bodily orifice is, in embodiments, a vagina or an anus/rectum of a subject. At least a portion of the hydrogen-delivering system, such as an elongate body, is configured to generate $H_2$ and to deliver $H_2$ to the tissues in the bodily orifice when the elongate body is removably disposed within the bodily orifice. Thus, in embodiments, a system, device, or an applicator is provided that is configured to be inserted into a bodily orifice to deliver molecular hydrogen in a targeted manner, directly to the tissues in the orifice. In embodiments, the subject is a human subject.

In embodiments, hydrogen-delivering systems relate to hydrogen storing and generating systems in which molecular hydrogen either stored on a surface of a system or its portion(s), or a chemical mixture inside of the system is activated either by absorption of moisture from the surface of a subject's vagina or an anal canal and rectum, or by the addition of aqueous solution to produce molecular hydrogen inside the system. The system (or device), which can be referred to as an "$H_2$-Tampon" or "HyTampon," is inserted into a subject's vagina or an anal canal and rectum to deliver molecular hydrogen diffused from the system into the body tissues through the adjacent surface, for therapeutic effect.

In embodiments, targeted hydrogen therapy is provided using several types of systems in accordance with the present disclosure. Thus, in some embodiments, a hydrogen nanobubbles-rich solution is prepared separately, and at least a portion of the system (such as an elongate body) is immersed in this solution and filled with hydrogen nanobubbles that accumulate on the surface of the elongate body. The soaked elongate body with accumulated molecular hydrogen is then placed in the vagina or anal canal and/or rectum of a subject for a therapeutic effect.

In some embodiments, a hydrogen-generating chemical reaction inside a system or a portion thereof (such as an elongate body that encompasses at least one dry compound) is activated during or before the application. The activation involves contacting dry $H_2$-generating compounds disposed inside the system's elongate body with a liquid (or at least partially liquid) activator. The elongate body, or a portion thereof including the dry $H_2$-generating compounds and in which an $H_2$-generating reaction takes place, can be referred to as a chemical chamber.

In embodiments, molecular hydrogen gas diffuses readily through the system's surface and penetrates the tissues in a bodily orifice, while other components of the hydrogen-generating chemical reaction, including in some embodiments the liquid activator (e.g., without limitation, an aqueous solution), remain inside the system (e.g., inside the elongate body). The molecular hydrogen gas arising during activation in an interior of the elongate body diffuses through the walls of the elongate body and penetrates into the tissues in the bodily orifice.

In embodiments in which a hydrogen-generating chemical reaction occurs inside a system's elongate body that includes dry $H_2$-generating compound(s) (referred to as "dry compounds" throughout this disclosure), upon contact of the dry compounds with a liquid activator, the liquid activator can be delivered to the dry compounds from a surrounding environment (e.g., from an external source). Thus, in some embodiments, at least the elongate body is immersed in the liquid activator, outside of the subject's body, to thereby activate the $H_2$-generating reaction. The elongate body is then inserted into the bodily orifice to deliver $H_2$ thereinto.

In some embodiments, the elongate body is inserted into the bodily orifice and absorbs bodily fluids, such as, without limitation, menstrual discharge (e.g., blood and vaginal secretions), serving as a liquid activator. As menstrual discharge or other biological fluids come in contact with the dry compounds disposed within the elongate body, the $H_2$-generating reaction occurs to thereby generate molecular hydrogen that diffuses from within the elongate body into tissues in the bodily orifice.

In some embodiments, a liquid activator is delivered to dry compounds disposed within the elongate body from an external source such as a container releasably holding therein the liquid activator, e.g., water, sodium chloride solution, calcium hydroxide solution, a buffer (e.g., phosphate buffered saline (PBS), Tris (tris(hydroxymethyl)aminomethane), HEPES (4-(2-hydroxyethyl)-1-piperazineethanesulfonic acid), etc., and variants thereof) or another suitable liquid or similar substance. The liquid activator is delivered to the dry compounds prior to insertion of the elongate body into the bodily orifice, or after the elongate body has been inserted into the bodily orifice. As the $H_2$-generating reaction occurs inside the elongate body, molecular hydrogen diffuses from within the elongate body into tissues in the bodily orifice.

Accordingly, in some aspects, a system for delivery of molecular hydrogen into a bodily orifice of a subject is provided. In embodiments, the system comprises a cylindrical, elongate body having proximal and distal ends extending between a longitudinal axis thereof and configured to be delivered into the bodily orifice. In embodiments, the system also comprises a pull element extending from the proximal end of the elongate body and configured to be at least partially disposed outside of the bodily orifice when the elongate body is inserted into the bodily orifice. In embodiments, the elongate body comprises an inner cavity having enclosed therein at least one dry compound capable of generating molecular hydrogen upon exposure to a liquid activator, and a barrier encompassing the at least one dry compound and that is at least partially hydrogen-permeable and not permeable to the at least one dry compound.

In embodiments, at least a portion of the elongate body can be expandable such that, when the elongate body is inserted into the bodily orifice, the elongate body expands to abut tissues in the bodily orifice.

In embodiments, the system is configured to have molecular hydrogen generated inside its elongate body and releases the generated molecular hydrogen to the outside of the elongate body, to thereby deliver the molecular hydrogen to tissues of the bodily orifice.

In some embodiments, the liquid activator comprises a bodily fluid that is transferred to the inner cavity through the barrier when the elongate body is inserted into the bodily orifice.

In some embodiments, the liquid activator is delivered to the at least one dry compound from an external source.

In some embodiments, the barrier is not permeable to the liquid activator such that the liquid activator delivered to the at least one dry compound from the external source is not released to the outside of the elongate body.

In some embodiments, the system comprises an enclosure disposed in the elongate body. In some embodiments, the system comprises an enclosure disposed in the inner cavity including the at least one dry compound. The enclosure is, in embodiments, coupled to an interior of the elongate body.

In some embodiments, the system comprises a tube connector extending between the elongate body and an activator fluid container such that the liquid activator, releasably disposed in the activator fluid container, is delivered to the at least one dry compound. In some embodiments, the system comprises the activator fluid container removably coupled to the elongate body via the tube connector.

In some embodiments, the activator fluid container is configured to be moved from a first, initial configuration to a second configuration to thereby release the liquid activator releasably disposed therein. For example, the activator fluid container can be configured to be moved to the second configuration upon pressure applied thereto.

In some embodiments, the tube connector comprises a distal portion that is coupled to the proximal end of the elongate body, and a proximal portion coupled to the activator fluid container, and wherein the proximal portion of the tube connector is configured to be decoupled from the distal portion of the tube connector after the liquid activator releasably disposed in the activator fluid container is delivered to the at least one dry compound, thereby disconnecting the activator fluid container from the elongate body.

In some embodiments, the pull element extending from the proximal end of the elongate body comprises the distal portion of the tube connector, i.e., the distal portion of the tube connector serves as the pull element.

In some embodiments, the pull element is separate from the tube connector.

In some embodiments, the liquid activator comprises menstrual discharge (e.g., blood) and/or other bodily fluids from the vagina.

In some embodiments, the elongate body is in the form of an anal suppository configured to be inserted into the bodily orifice comprising an anal canal and/or rectum.

In some embodiments, the system is configured to be self-administered. In some embodiments, the system, or its portion (e.g., an elongate body and/or an activator fluid container) is enclosed in a removable package that is removed before use of the system. The removable package is, in embodiments, configured to facilitate insertion of the elongate body into the bodily orifice. The removable package can include one or more components. For example, it can include an applicator facilitating insertion of the elongate body into the bodily orifice, and an outer packaging that protects the system prior to use.

In some aspects, a method of delivering molecular hydrogen to tissues in a bodily orifice of a subject is provided. The method comprises inserting into the bodily orifice an elongate body configured to generate molecular hydrogen, wherein the elongate body has enclosed in an inner cavity thereof at least one dry compound capable of generating molecular hydrogen upon exposure to a liquid activator, and wherein the elongate body has a pull element coupled to a proximal end thereof. The method further comprises allowing the at least one dry compound included in the elongate body generate the molecular hydrogen upon exposure to the liquid activator to thereby deliver the molecular hydrogen to tissues in the bodily orifice, and, after a time period, pulling the pull element proximally to thereby withdraw the elongate body from the bodily orifice after the molecular hydrogen is delivered to the tissues in the bodily orifice.

In some embodiments, the method further comprises delivering the liquid activator to the inner cavity of the elongate body such that the one dry compound is contacted with the liquid activator thereby generating the molecular hydrogen that is released from the elongate body. In some embodiments, the liquid activator comprises a bodily fluid that is transferred to the inner cavity when the elongate body is inserted into the bodily orifice.

In some embodiments, the elongate body comprises an outer absorbent layer, and an inner layer that is at least partially hydrogen-permeable and not permeable to the at least one dry compound, and wherein the outer absorbent layer absorbs and retains the bodily fluid when the elongate body is inserted into the bodily orifice.

In some embodiments, the liquid activator is delivered to the inner cavity from an external source. In some embodiments, the external source can comprise an activator fluid container releasably storing therein the liquid activator and being removably coupled to the elongate body via a tube connector that is configured to deliver the liquid activator from the activator fluid container to the at least one dry compound within the elongate body.

In some embodiments, the method comprises causing the activator fluid container to release the liquid activator that is delivered to the at least one dry compound within the elongate body.

In some embodiments, the method comprises removing the activator fluid container after the liquid activator is delivered to the at least one dry compound. In some embodiments, the method comprises removing the activator fluid container after the liquid activator is delivered to the at least one dry compound and the at least one dry compound generates the molecular hydrogen. The activator fluid container can be decoupled from the elongate body after the liquid activator is delivered to the at least one dry compound.

In some embodiments, the time period during which the system is being administered to the bodily orifice such that the elongate body remains inserted in the orifice, comprises at least 5 minutes, or at least 10 minutes, or at least 15 minutes, or at least 20 minutes, or at least 25 minutes, or at least 30 minutes, or at least 45 minutes, or at least one hour. In some embodiments, the time period comprises at least one hour, or at least 2 hours, or at least 3 hours, or at least 4 hours, or at least 5 hours, or at least 6 hours, or at least 7 hours, or at least 8 hours.

In some embodiments, the method comprises delivering from about 0.25 mmol (millimole) to about 2 mmol of the molecular hydrogen to tissues in the bodily orifice. In some embodiments, the method comprises delivering at least about 0.25 mmol, or at least about 0.5 mmol, or at least about 0.75 mmol, or at least about 1 mmol, or about 0.25 mmol, or about 0.5 mmol, or about 0.75 mmol, or about 1 mmol of molecular hydrogen.

In some embodiments, the method comprises alleviating or preventing dysmenorrhea (e.g., primary and/or secondary dysmenorrhea). The method allows alleviating or preventing dysmenorrhea, such as cramps, lower abdominal pain, lower back pain, diarrhea, headache, nausea, dizziness, and other types of symptoms causing discomfort and, in some cases, even disruption of normal daily activity.

In some embodiments, the method comprises treating a wound in the bodily orifice. The wound, in embodiments, comprises cuts, scrapes, scratches, lacerations, avulsions, and abrasions in the anus and rectum, or in the vagina. In some embodiments, the method comprises treating or preventing scars.

In some embodiments, an outer surface of the elongate body is covered with an additional agent, wherein the additional agent optionally comprises one or more of a moisturizer, a disinfectant, therapeutic agent, and a lubricant.

In some aspects, a method of delivering molecular hydrogen to tissues in a bodily orifice of a subject is provided. The method comprises preparing a hydrogen solution comprising molecular hydrogen; placing an elongate body having an absorbent outer layer into the hydrogen solution such that at least the outer layer absorbs the solution comprising the molecular hydrogen, wherein the elongate body has a pull element coupled to a proximal end thereof; inserting into the bodily orifice the elongate body with at least the outer layer having absorbed the hydrogen solution, for a time period that allows the molecular hydrogen be released from the elongate body and delivered to tissues in the bodily orifice; and, after the time period, pulling the pull element proximally to thereby withdraw the elongate body from the bodily orifice.

In some embodiments, the hydrogen solution is prepared by dissolving at least one solid form in an aqueous activator, wherein the at least one solid form is capable of generating molecular hydrogen upon contact with the aqueous activator. In some embodiments, at least one solid form comprises a pill, tablet, or powder. In some embodiments, the aqueous activator comprises water.

In some embodiments, the time period comprises at least 5 minutes, or at least 10 minutes, or at least 15 minutes, or at least 20 minutes, or at least 25 minutes, or at least 30 minutes, or at least 45 minutes, or at least one hour.

BRIEF DESCRIPTION OF THE DRAWINGS

Non-limiting embodiments of the present disclosure will be described by way of example with reference to the accompanying figures, which are schematic and are not intended to be drawn to scale. The drawings illustrate exemplary embodiments of the present disclosure and do not therefore limit its scope. In the figures, each identical or nearly identical component illustrated is typically represented by a single numeral. For purposes of clarity, not every component is labeled in every figure, nor is every component of each embodiment of the present disclosure shown where illustration is not necessary to allow those of ordinary skill in the art to understand the present disclosure. In the figures:

FIG. 3A is a perspective view of a hydrogen-delivering system in accordance with embodiments of the present disclosure, in which a liquid activator is delivered to an elongate body from an external source.

FIG. 3B is a partial, exploded view of the hydrogen-delivering system of FIG. 3A.

FIG. 3C is a partial, longitudinal cross-sectional view of the elongate body of the hydrogen-delivering system of FIG. 3A.

FIG. 4 is a partially transparent, longitudinal cross-sectional view of a hydrogen-delivering system in accordance with embodiments of the present disclosure, wherein an elongate body is configured to receive a liquid activator from an external source and wherein a distal portion of a tube connector extending between the elongate body and the external source functions as a pull element after the liquid activator is delivered to the elongate body.

FIG. 5 is a partially transparent, longitudinal cross-sectional view of a hydrogen-delivering system in accordance with embodiments of the present disclosure, wherein an elongate body is configured to receive a liquid activator from an external source, and comprising a pull element that is separate from a tube connector.

Figure 2A:
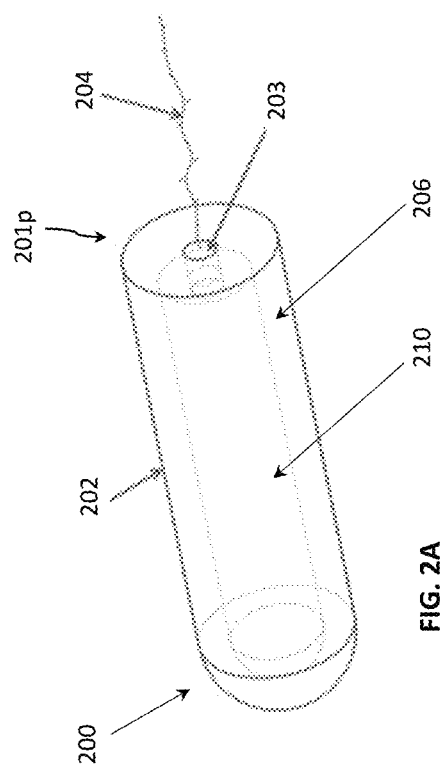
FIG. 2A is a partially transparent view of a hydrogen-delivering system in accordance with embodiments of the present disclosure, wherein an elongate body is configured to absorb a biological fluid from tissues of a bodily orifice of a subject.

The drawings are not intended to be limiting in any way, and it is contemplated that various embodiments of the present disclosure may be carried out in a variety of other ways, including those not necessarily depicted in the drawings. The accompanying drawings incorporated in and forming a part of the specification illustrate several aspects of the present invention, and together with the description serve to explain the principles of the present disclosure; it being understood, however, that embodiments of the present disclosure is not limited to the precise arrangements shown.

DETAILED DESCRIPTION

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The present disclosure provides a hydrogen-delivering system and method for delivery of molecular hydrogen ($H_2$) in a bodily orifice of a subject. In some embodiments, the bodily orifice can be a vagina, and the system (e.g., a tampon) can be sized and shaped to fit a vagina such that the system, once inserted into the vagina, delivers molecular hydrogen into tissues of the vagina. The molecular hydrogen nourishes the walls of the vagina, heals lacerations, relieves menstrual cramps, premenstrual syndrome symptoms, etc.

In some embodiments, the bodily orifice is anus/rectum, and the hydrogen-delivering system comprises an anal applicator or suppository configured to deliver $H_2$ to tissues in the subject's anus and rectum. Various wounds within the anus and/or rectum can be treated, and pain can be alleviated.

Existing methods for delivering of molecular hydrogen to a patient's body include administration of $H_2$ inhalations, oral administration of hydrogen-infused liquids (e.g., $H_2$-enriched water, $H_2$-infused saline, etc.) or hydrogen-releasing solids (e.g., capsules or tablets), injecting $H_2$-containing solutions (e.g., intravenous injections), $H_2$-enriched baths, and other ways of delivering hydrogen to the subject's body. These methods have their advantages and disadvantages and serve for certain purposes of healing and therapy. Systems and methods that make use of the effects of molecular hydrogen on the skin are described in U.S. patent application Ser. No. 16/376,894, filed on Apr. 5, 2019, the entire disclosure of which is incorporated herein by reference. Beneficial effects of $H_2$ in the clinical environment were reported, demonstrating its role as a therapeutic agent in medicine. See Ostojic, *F1000Research* vol. 5 2659. 10 Nov. 2016, doi:10.12688/f1000research.9758.1. Usually administered orally or via inhalation, $H_2$ improves both patient- and clinician-reported outcomes, and biomarkers of different pathologies and disorders, from metabolic diseases to chronic systemic inflammatory disorders to cancer. See id. Furthermore, studies have shown that molecular hydrogen exerts antioxidant, anti-apoptotic, anti-inflammatory, and cytoprotective properties that are beneficial to the cell. See Dixon et al., *Med Gas Res.* 2013 May 16; 3(1):10. doi: 10.1186/2045-9912-3-10.

Aspects of the present disclosure make use of unique properties of molecular hydrogen as a therapeutic agent. A system or device in accordance with embodiments of the present disclosure can deliver $H_2$ into a bodily orifice of a subject, as a safe therapy for prevention and treatment of various conditions and symptoms, as well as for treatment of wounds. The system can be configured for vaginal or anal/rectal use.

In some aspects, a system for delivery of molecular hydrogen into a bodily orifice of a subject is provided that comprises a cylindrical, elongate body having proximal and distal ends extending between a longitudinal axis thereof, and configured to be delivered into the bodily orifice. The elongate body can comprise an inner cavity having enclosed therein at least one dry compound capable of generating molecular hydrogen upon exposure to a liquid activator, a barrier encompassing the at least one dry compound and that is at least partially hydrogen-permeable and not permeable to the at least one dry compound, and a pull element extending from the proximal end of the elongate body and configured to be at least partially disposed outside of the bodily orifice when the elongate body is inserted into the bodily orifice.

In embodiments, the system for delivery of molecular hydrogen into a bodily orifice of a subject can be interchangeably referred to as a device.

As used herein, "cylindrical" refers to an elongate body that is generally cylindrical. The elongate body can however have other shapes, and it can have features (e.g., grooves, ridges, wings, extensions, etc.) that can make it deviate from the cylindrical shape. Also, the shape of the elongate body can change as it at least partially expands within the subject's bodily orifice, as it absorbs bodily fluids or other fluid(s) acting as a liquid activator, and/or as it generates molecular hydrogen. In some embodiments, the elongate body is substantially cylindrical. Regardless of its specific configuration, the elongate body of a system in accordance with embodiments of the present disclosure is sized and shaped to fit a bodily orifice.

Further, as used herein, a "bodily orifice" collectively refers to both an orifice (opening) in a subject's body and a bodily cavity to which that orifice opens. Thus, the bodily orifice is, in embodiments, the vagina, and an elongate body of a system in accordance with the present disclosure is configured to be inserted into the vagina through the vaginal opening. In embodiments, the bodily orifice is the anus, and an elongate body of a system in accordance with the present disclosure is configured to be inserted into the anal canal (which is the terminal segment of the large intestine, between the rectum and anus) via the anus. In embodiments, an elongate body is inserted into a subject's body via the anus and into the rectum—i.e., the elongate body is seated deeper in the subject's large intestine, such that it is positioned in both the anal canal and rectal canal. In addition, in embodiments in which a subject is undergoing or has undergone a sex reassignment surgery or another type of body-changing surgery, an elongate body is configured to be inserted into a bodily orifice that is a surgically reconstructed vagina.

Also, although embodiments of the present disclosure described herein refer to a hydrogen-generating system, it should be appreciated that the system can also be referred to as a device, applicator, or in other ways. The system is configured for application (insertion) into the genitals, vagina, or an anal canal and rectum to deliver $H_2$ thereto.

In some embodiments, the liquid activator comprises a bodily fluid that is transferred to the inner cavity of the elongate body through the barrier when the elongate body is inserted into the bodily orifice. It should be appreciated that the liquid activator does not have to be fully liquid, as it can be an at least partially viscous, colloidal, or semifluid substance. Also, bodily fluids from the bodily orifice can have various particles, fragments and other elements that are not necessarily liquid. Thus, for the purposes of the present disclosure, the liquid activator refers to an activator fluid, solution, suspension, or other type of activator that delivers moisture to initially dry $H_2$-generating compound(s) that is sufficient to cause the $H_2$-generating dry compounds generate molecular hydrogen.

In some embodiments, the elongate body comprises an outer absorbent layer, and an inner layer at least partially encompassing the inner cavity, wherein the inner layer comprises the barrier, and wherein at least the outer absorbent layer absorbs and retains the bodily fluid when the elongate body is inserted into the bodily orifice. In some embodiments, the inner layer is also absorbent.

In embodiments, the elongate body is formed at least in part from viscose, cotton, or similar absorbent material(s). The outer, tissue-facing surface of the elongate body, which may come in contact with tissues lining the bodily orifice, is soft and not traumatic to the tissues.

In some embodiments, the liquid activator is delivered to the at least one dry compound from an external source. The external source can be a container, which can be removably coupled to the elongate body, or it can be a separate container.

Furthermore, in some embodiments, exposing at least one dry compound to a liquid activator from an external source comprises placing at least the elongate body (having the at least one dry compound) of the system into a liquid activator such that the elongate body absorbs the liquid activator from the surrounding environment.

In some embodiments, the barrier encompassing the at least one dry compound is not permeable to the liquid activator such that the liquid activator delivered to the at least one dry compound from the external source is not released to the outside of the elongate body.

In embodiments in which the liquid activator is biological fluid(s) delivered to the at least one dry compound from a surrounding environment, the barrier encompassing the at least one dry compound is permeable to the liquid activator such that the biological fluids pass from the outside of the elongate body, through the barrier, and towards the at least one dry compound.

In some embodiments, the barrier is formed by an inner wall of the elongate body forming the inner cavity.

In some embodiments, the system further comprises a cover disposed at the proximal end of the elongate body. In some embodiments, the cover has a pull element coupled thereto. The pull element can be or can comprise a string (e.g., a fabric string or another type of string that is comfortable for subject's use). In some embodiments, the pull element is coupled to the elongate body in other ways. For example, the pull element can be sewn into the elongate body (e.g., into the fabric of the elongate body), or coupled to the elongate body and/or any of its features in other ways.

In some embodiments, the system further comprises a reservoir or enclosure disposed in the inner cavity and having the barrier such that the enclosure includes the at least one dry compound. In some embodiments, the enclosure is coupled to an interior of the elongate body. For example, the enclosure can be coupled to a wall of the inner cavity.

In some embodiments, the elongate body is formed from an absorbent material, and the enclosure is disposed along the longitudinal axis of the elongate body. In some embodiments, the enclosure is disposed centrally along the longitudinal axis of the elongate body. In some embodiments, the enclosure can be embedded within the material(s) forming the elongate body.

In some embodiments, the enclosure is integrally formed with at least a portion of the elongate body. In some embodiments, the enclosure can be formed within the interior of the elongate body. For example, when at least the outer portion (e.g., a layer) or the entire elongate body is formed from an absorbent material, the enclosure encompassing the dry compounds for $H_2$ generation can be inserted into the elongate body. In some embodiments, the inner cavity is not a separate cavity or chamber formed in the elongate body. Rather, the inner cavity is formed by virtue of the enclosure being inserted into the elongate body. The enclosure can be inserted along a longitudinal axis of the elongate body (e.g., centrally along the longitudinal axis of the elongate body). The enclosure can be inserted in other ways within the elongate body, which may depend on a size and shape of the enclosure and the elongate body. Also, as discussed in more detail below, the elongate body can encompass more than one enclosure with dry compound(s).

In some embodiments, as mentioned above, a liquid activator can be delivered into the elongate body, to contact the dry compounds, from an external source. The external source can be initially part of the system and it can be removed from the system after the liquid activator is delivered to the interior of the elongate body. The external source can be, for example, an activator fluid container configured to releasably store therein the liquid activator.

In some embodiments, for example, in which the system is manufactured as a kit, the external source, such as an activator fluid container, can be a separate component releasably storing the liquid activator. The system can be reversibly connected to the component storing the liquid activator and then disconnected from the component once the liquid activator is delivered to the dry compounds within the hydrogen-delivering system. In some embodiments, the kit includes an activator fluid container that is configured to be removed from the system upon delivery of the liquid activator from the activator fluid container to the dry compounds within the hydrogen-delivering system.

In embodiments, the activator fluid container can have various configurations, sizes, and shapes, and it can be formed from various materials. In some embodiments, the activator fluid container is configured to be moved from a first, initial configuration to a second configuration to thereby release the liquid activator releasably disposed therein. In some embodiments, the activator fluid container is configured to be moved to the second configuration upon pressure applied thereto. For example, the activator fluid container can be made from at least partially pliable material, or another type of a material that allows squeezing, pressing upon, or otherwise manipulating the activator fluid container to cause it to release the liquid activator. The activator fluid container can be a bag, pouch, sac, or any other type of a container. The container can have various sizes and shapes, and it can be connected to the elongate body of the system in various ways.

In some implementations, the activator fluid container can include an opener or another feature that assists in releasing a liquid activator from the activator fluid container.

In some embodiments, the system has a tube connector extending between the elongate body and an activator fluid container such that the liquid activator releasably disposed in the activator fluid container is delivered to the at least one dry compound. The activator fluid container can be removably coupled to the elongate body via the tube connector. The tube connector can comprise a valve and/or other components that allow the liquid activator to flow from the activator fluid container to the elongate body.

In some embodiments, the tube connector comprises a distal portion that is coupled to the proximal end of the elongate body, and a proximal portion coupled to the activator fluid container. Prior to use, the distal and proximal portions of the tube connector form a connection between the activator fluid container and the system. In these embodiments, the proximal portion of the tube connector is configured to be decoupled from the distal portion of the tube connector after the liquid activator releasably disposed in the activator fluid container is delivered to the at least one dry compound. For example, a connection between the distal and proximal portions can be frangible such that the user (which is, in some embodiments, a subject who is self-administering the system) can separate the proximal portion of the tube connector (having the activator fluid container coupled thereto) from the distal portion, thereby disconnecting the activator fluid container from the elongate body. This can occur when the elongate body is positioned in the bodily orifice. Also, in some cases, the hydrogen-generating reaction can be initiated in the elongate body before the elongate body is inserted into the bodily orifice (e.g., about 1-5 minutes, or about 1-10 minutes, or about 10 minutes, or about 5 minutes, or about 3 minutes, or about 1 minute, or less than about 10 minutes, or less than about 5 minutes, or less than about 3 minutes, or less than about 1 minute prior to the insertion). Molecular hydrogen is generated within the elongate body when the elongate body or system is said to be "activated" such that a liquid activator is brought in contact with dry hydrogen-generating and/or hydrogen-storing compounds disposed in the elongate body.

In embodiments in which the proximal and distal portions of the tube connector are separable from one another, the distal portion of the tube connector, remaining coupled to the elongate body, can serve as the pull element. In such embodiments, the distal portion remains at least partially outside the subject's body while the system is in use, i.e. as it delivers $H_2$ to tissues in the bodily orifice, as well as, in some embodiments, used to absorb fluids from the bodily orifice. The distal portion in the form of the pull element can then be used to remove the elongate body from the bodily orifice (e.g., by pulling the distal portion away from the bodily orifice).

In some embodiments, as discussed below, the elongate body has both a pull element and a tube connector extending between the elongate body and the activator fluid container. In such embodiments, the pull element is separate from the tube connector.

It should be appreciated that the tube connector can have any suitable configuration and size, and it can have shapes that are different from a tube. Regardless of its specific configuration, the tube connector provides a fluidic communication between the elongate body (more specifically, the dry compounds capable of generating $H_2$) and the activator fluid container.

In embodiments, at least a portion of the elongate body is expandable such that, when the elongate body is inserted into the bodily orifice, the elongate body expands to abut tissues in the bodily orifice. In this way, the elongate body sits reliably and comfortably within the bodily orifice, until an action is taken to withdraw it from the orifice. The elongate body can be formed from a soft, resiliently expandable material that is comfortable to the subject. The elongate body can change its shape to a certain degree, to adjust based on the shape inside the bodily orifice.

In some embodiments, at least a portion of the elongate body expands when the at least one dry compound is exposed to the liquid activator thereby generating the molecular hydrogen. In some embodiments, at least a portion of the elongate body expands upon exposure to moisture in the bodily orifice. In some embodiments, additionally, at least a portion of the elongate body expands once when elongate body is released from its packaging where it can be placed in a partially compressed form such that, once released from the packaging into the bodily orifice, the elongate body expands.

In embodiments, the elongate body can have various shapes and sizes. In some embodiments, the elongate body has both ends curved and of approximately the same (e.g., rounded) shapes. In some embodiments, the proximal end is cut under a straight angle, whereas the distal end is convex and shaped for a convenient and comfortable to the subject insertion into the subject's body. In some embodiments, the proximal end of the elongate body is also curved but to a lesser degree than the distal end. Embodiments of the present disclosure are not limited to a specific shape of the elongate body.

In some embodiments, the proximal end of the elongate body is proximally tapered.

In embodiments, the elongate body is in the form of a tampon configured to be inserted into the bodily orifice comprising a vagina. The liquid activator comprises menstrual blood and/or bodily fluids from the vagina.

In embodiments, the elongate body is in the form of an anal suppository configured to be inserted into the bodily orifice comprising an anal canal and/or rectum.

In embodiments, the elongate body is configured to be self-administered. Thus, the system is suitable for at-home use. In some embodiments, the system or its portion (e.g., the elongate body) is enclosed in a removable package that is removed before use of the system. In some embodiments, the removable package is configured to assist insertion of the elongate body into a bodily orifice of the subject.

In some aspects, a method of delivering molecular hydrogen to tissues in a bodily orifice of a subject is provided. The method comprises inserting into the bodily orifice an elongate body configured to generate molecular hydrogen, wherein the elongate body has enclosed in an inner cavity thereof at least one dry compound capable of generating molecular hydrogen upon exposure to a liquid activator, and wherein the elongate body has a pull element coupled to a proximal end thereof. In embodiments, the method further comprises allowing the at least one dry compound included in the elongate body generate the molecular hydrogen upon exposure to the liquid activator to thereby deliver the molecular hydrogen to tissues in the bodily orifice, and, after a time period, pulling the pull element proximally to thereby withdraw the elongate body from the bodily orifice after the molecular hydrogen is delivered to the tissues in the bodily orifice.

In some embodiments, the time period during which the elongate body remains in the bodily orifice as molecular hydrogen is released therefrom comprises at least 5 minutes, or at least 10 minutes, or at least 15 minutes, or at least 20 minutes, or at least 25 minutes, or at least 30 minutes, or at least 45 minutes, or at least one hour. In some embodiments, the time period is about 5 minutes, or about 10 minutes, or about 15 minutes, or about 20 minutes, or about 25 minutes, or about 30 minutes, or about 45 minutes, or about an hour. In some embodiments, the time period is about 1 minute, or is less than 1 minute.

In some embodiments, the elongate body, e.g., in the form of a vaginal tampon, can remain in the subject's body for the duration of time similar to the time allowed for a conventional tampon—e.g., up to 8 hours. Thus, in some embodiments, the time period comprises at least one hour, or at least 2 hours, or at least 3 hours, or at least 4 hours, or at least 5 hours, or at least 6 hours, or at least 7 hours, or at least 8 hours. It should be appreciated, however, that therapeutic benefits of molecular hydrogen produced by the activated system can last for a shorter time period—e.g., up to about 30 minutes. The time period may depend on a type of the system, a condition being treated, and other factors.

The amount of molecular hydrogen generated by the system in accordance with embodiments of the present disclosure is sufficient to provide desired therapeutic effect.

In some embodiments, the method can alleviate or prevent dysmenorrhea. In some embodiments, the method can be used to treat hemorrhoids. In some embodiments, the method can be used to treat anal fissures and other anorectal conditions or diseases.

In some aspects, a method of delivering molecular hydrogen to tissues in a bodily orifice of a subject is provided. The method comprises preparing a hydrogen solution comprising molecular hydrogen; placing an elongate body having an absorbent outer layer into the hydrogen solution such that at least the outer layer absorbs the solution comprising the molecular hydrogen. The elongate body has a pull element coupled to a proximal end thereof. In embodiments, the method comprises inserting into the bodily orifice the elongate body with at least the outer layer having absorbed the hydrogen solution, for a time period that allows the molecular hydrogen be released from the elongate body and delivered to tissues in the bodily orifice. The method further comprises, after the time period, pulling the pull element proximally to thereby withdraw the elongate body from the bodily orifice.

In some embodiments, the hydrogen solution is prepared by dissolving at least one solid form in an aqueous activator, wherein the at least one solid form is capable of generating molecular hydrogen upon contact with the aqueous activator. In embodiments, the at least one solid form comprises, without limitation, a pill, tablet, pellet, dry powder (which can be homogeneous, heterogeneous, or compressed powder), flakes, or any other solid form.

In some embodiments, the aqueous activator comprises water. The liquid activator can also be a sodium chloride solution, a food-grade water suspension of food-grade calcium hydroxide, etc.

In some embodiments, the time period comprises at least 5 minutes, or at least 10 minutes, or at least 15 minutes, or at least 20 minutes, or at least 25 minutes, or at least 30 minutes, or at least 45 minutes, or at least one hour.

In some embodiments, the outer surface of the elongate body is covered with an additional agent, wherein the additional agent optionally comprises one or more of a moisturizer, a disinfectant, a therapeutic agent, and a lubricant. In some embodiments, the additional agent is a therapeutic agent. The additional agent can be anesthetic or analgesic agent. As molecular hydrogen is generated, molecular diffusion forces of hydrogen cause the molecules of the therapeutic agent to be transferred to the tissues of the bodily orifice to provide a desired therapeutic effect.

In various embodiments, as mentioned above, the system is in the form of a tampon, such as a sanitary tampon used by subjects during menstruation. The primary purpose of a typical sanitary tampon is to absorb menstrual fluids and provide certain comfort, with obstruction of secretions from the vagina. A tampon is described, for example, in U.S. Pat. No. 6,533,771, which is incorporated by reference herein in its entirety. The present invention improves upon a sanitary tampon by providing a system that can both absorb menstrual and/or any other fluids from the vagina, and that can deliver molecular hydrogen to tissues within the vagina, thereby delivering a targeted therapeutic effect of the molecular hydrogen. In some embodiments, the tampon can be used at any time, regardless of whether or not a subject has menstruation (period), for example, when the subject is experiencing a premenstrual syndrome (PMS). In this way, embodiments of the present disclosure allow alleviation or prevention of dysmenorrhea, such as cramps, lower abdominal and lower back pain, diarrhea, headache, nausea, dizziness, vomiting, and other symptoms causing discomfort and even disruption of daily activity. See, e.g., Harel (2006). *J Pediatr Adolesc Gynecol.* 2006 December; 19(6):363-71; Negriff et al., *J Health Psychol.* 2009; 14(7):899-908; see also Singh et al., *Indian J Physiol Pharmacol* 2008; 52 (4): 389-397.

In some embodiments, a system and method of using the same, in accordance with the present disclosure, allow alleviation or prevention of symptoms of premenstrual syndrome (PMS).

In embodiments, dysmenorrhea can be defined as a combination of at least abdominal pain, negative affect/somatic complaints, and back pain. See Negriff et al., *J Health Psychol.* 2009; 14(7):899-908. Dysmenorrhea is a common health problem which is thought to occur, for example, in between 50 percent and 91 percent of young women. See id. Furthermore, dysmenorrhea may be categorized into two types: primary and secondary. Primary dysmenorrhea is defined as painful menses, as well as presence of other symptoms, in women with normal pelvic anatomy (usually beginning during adolescence), whereas secondary dysmenorrhea is menstrual pain associated with underlying pathology, and its onset may be years after menarche. See Unsal et al. *Upsala journal of medical sciences* vol. 115, 2 (2010): 138-45.

Dysmenorrhea is typically related to the symptoms of pain accompanying menses, and PMS is generally focused on the emotional or psychological concerns (though there is an overlap in the symptoms of both of these menstrual-related diagnoses). See Negriff et al. (2009). Common PMS somatic symptoms include breast tenderness, abdominal bloating, headache, and swelling of extremities. See id.; see also American College of Obstetricians and Gynecologists. ACOG Compendium of selected publications, Washington, D.C.: The American College of Obstetricians and Gynecologists; 2000. ACOG Practice Bulletin: Premenstrual syndrome; pp. 1057-1064. Also, PMS symptoms begin before the menstrual cycle and resolve shortly after menstrual flow begins. Coco (1999). *Am Fam Physician;* 60: 489-496.

In embodiments, a subject has dysmenorrhea when the subject is experiencing one or more of cramps, lower abdominal and lower back pain, diarrhea, headache, nausea, dizziness, vomiting, and other types of symptoms. In some embodiments, the one or more symptoms of dysmenorrhea are reduced. In some embodiments, the one or more symptoms of dysmenorrhea are reduced or prevented.

In embodiments, severity of dysmenorrhea (e.g., primary and/or secondary dysmenorrhea) is reduced. The severity of dysmenorrhea can be defined in various ways. For example, in some embodiments, the severity of dysmenorrhea is defined based on a scoring system that is based on subjects' self-assessment. The more severe dysmenorrhea is typically associated with more pronounced symptoms, such as, e.g., pain and cramps, and with less responsiveness to analgesics. In some embodiments, for example, mild (grade 1) dysmenorrhea is defined as: menstruation is painful but seldom inhibits normal activity, analgesics are seldom required, mild pain; moderate (grade 2) dysmenorrhea is defined as: daily activity is affected, analgesics required and give sufficient relief so that absence from school or work is unusual, moderate pain; and severe (grade 3) dysmenorrhea is defined as: activity clearly inhibited, poor effect of analgesics, vegetative symptoms (headache, fatigue, vomiting, and diarrhea), severe pain. See Unsal et al. (2010).

In embodiments, a severity of dysmenorrhea is reduced such that the subject's dysmenorrhea is reduced from a more severe grade to a less severe grade. For example, dysmenorrhea can be reduced from severe to moderate or mild, or from moderate to mild, or from mild to zero-symptom dysmenorrhea. Continuing with the example above, a zero (0) grade dysmenorrhea is, in embodiments, defined as a scenario when menstruation is not painful and daily activity is unaffected. See Unsal et al. (2010). A system and method of using the same in accordance with embodiments of the present disclosure allow reducing the symptoms of dysmenorrhea in a subject such that the subject is experiencing fewer and/or lesser symptoms (or no symptoms) than the symptoms that the subject experienced before using the present system, or than subjects that are not using the present system.

In some embodiments, a severity of dysmenorrhea is assessed by Visual Analogue Scale (VAS) which is a standard pain assessment tool. See Amirkhani et al., *Journal of Family and Reproductive Health* 2012; 6(3):95-98. According to this scale, zero indicates "no feeling of pain" and 10 denotes "severe pain." See Unsal et al., Pakistan Journal of Medical Sciences 2010; 26(1):142-147. See also Khodakarami et al. *J Midwifery Report Health.* 2015; 3(4):444-450. Thus, in some embodiments, a severity of dysmenorrhea is reduced such that pain associated with the subject's dysmenorrhea is reduced from a higher score to a lower score. The dysmenorrhea can be primary or secondary.

In some embodiments, a hydrogen-delivering system is in the form of an anal tampon, suppository, or applicator suitable for insertion into the anal canal and rectum of a subject. When configured for use as an anal suppository, the system in accordance with embodiments of the present disclosure helps treat various wounds, including cuts, scrapes, scratches, lacerations, avulsions, and abrasions in the anus and rectum. The wounds can also include small punctures that do not require surgical involvement. The system and method of use thereof can be used to treat anal fissures and other types of sores (ulcers) of the anus and rectum.

A system in accordance with embodiments of the present disclosure can also be used to treat various wounds in the vagina, such as, without limitation, cuts, scrapes, scratches, lacerations, avulsions, and abrasions in the vagina. The wounds can also include small punctures that do not require surgical involvement.

The system can be in the form of any other type of applicator suitable for insertion to a vagina or anus/rectum. In embodiments, the system is configured specifically for use in the vagina, or specifically for use in the anus/rectum. In some embodiments, the system is suitable for either use in the vagina or the use in the anus/rectum of a subject.

In some embodiments, a system in accordance with embodiments of the present disclosure can be used to help treat scars in the anus or vagina. The system can be used after a surgery on a bodily orifice (e.g., after the sutures or stitches have been removed and it is safe to insert an elongate body into the bodily orifice). The surgery can be an anal or rectal surgery, or a vaginal surgery. The vaginal surgery is, in embodiments, a vaginal cosmetic and reconstructive surgical procedure, a vaginoplasty as part of gender confirmation surgery (e.g., sex reassignment surgery or genital reassignment surgery), or other type of surgery. In some embodiments, the system and method of use thereof can be used after a vaginal childbirth, to help heal the vaginal area after delivery. Non-limiting examples of anal and/or rectal surgery include rectal prolapse surgery, hemorrhoidectomy, internal sphincterotomy, treatment of anal abscesses and fistulas, repair of a fissure, repair of sphincter injuries, polypectomy, and ileal pouch anal anastomosis (J-Pouch).

Regardless of its specific configuration, in a hydrogen-delivering system in accordance with embodiments of the present disclosure, all substances, including the dry compound(s) and in some embodiments a liquid activator, are in a closed space inside the elongate body, have no direct contact with tissues or skin, and are therefore safe and do not cause side effects. The hydrogen-delivering system is thus safe, easy to use, transport and store, and can be self-administered. In embodiments, the system is disposable.

In some embodiments, a hydrogen solution (e.g., hydrogen nanobubble-rich solution) with a concentration of molecular hydrogen from about 1 ppm (parts per million) to about 4 ppm is prepared separately from an $H_2$-delivering system. After the hydrogen nanobubbles solution is prepared, the hydrogen-delivering system is immersed in the hydrogen nanobubbles solution, and, once soaked with molecular hydrogen, is placed in a bodily orifice. In embodiments, hydrogen nanobubbles in large quantities are formed upon instant dissolution of dietary mixtures-based tablets, powders, or other solid forms in aqueous solutions. Upon dissolution of the solid forms, they react with an aqueous solution to thereby produce hydrogen nanobubbles, as described, for example, in Safonov & Khitrin, *Colloids and Surfaces A: Physicochem, Eng. Aspects,* 2013, vol. 436, pp. 333-336, which is incorporated by reference herein in its entirety.

In embodiments, a non-limiting example of a solid form comprises a powder called MagH2, the product of Nano H2 Minus, Inc. (Henderson, Nev.). This dietary product is described, e.g., in U.S. Pat. No. 8,852,660, which is incorporated by reference herein in its entirety.

In practice, electrolysis with a particular form of cathodes can also produce a saturated hydrogen nanobubbles solution. However, the method that involves the use of electrolysis is significantly more complicated, and requires specialized equipment. It thus would not be suitable for home use, for example. The approach provided by embodiments of the present disclosure overcomes the disadvantages of electrolysis-based approaches.

In embodiments, a system can be configured to both absorb bodily fluids (e.g., menstrual discharge) and to deliver molecular hydrogen, or it can be used specifically for $H_2$ delivery. In addition, in embodiments, the system can include additional agents, including therapeutic agents, which can be disposed inside the system and/or outside the system.

In some embodiments, a system in accordance with embodiments of the present disclosure includes dry compounds configured to release or generate $H_2$ upon contact with a liquid activator. An example of the dry compounds includes, without limitation, aluminum (e.g., a foil, flakes, powder (e.g., compressed powder), etc.) covered by aluminum oxide. Another example includes metallic magnesium, which can also be in the form of a foil, flakes, powder, or in any other form suitable for inclusion into a tampon or suppository. The dry compounds can be based or can include Ca, Mg, Al, Zn, Si, and/or Fe, and they are included in the system in the way that allows generating $H_2$ in a safe manner, so that only the molecular hydrogen is delivered to the tissues in the bodily orifice, while the compounds (as well as residues from a hydrogen-generating reaction) remain inside the system and do not come in contact with the tissues. In embodiments, the hydrogen-generating or hydrogen-releasing (collectively referred to as "hydrogen-generating") compounds are dry prior to their activation upon exposure to a liquid activator. As the compound are exposed to moisture from an activator, they generate molecular hydrogen.

In some embodiments, a hydrogen-generating system is activated to release $H_2$ using a liquid activator such as, e.g., a water-based solution, introduced into the system from an external source. The system can be activated before the system (or a part of it, such as an elongate body) is inserted into a bodily orifice, or after the elongate body of the system is positioned in the bodily orifice. A hydrogen-generating reaction that occurs inside the system generates molecular hydrogen for a certain period of time, and the hydrogen diffuses from within the system to the tissue inside the vagina or inside the anal canal and rectum.

The liquid activator can be biological fluid(s) from the bodily orifice having the system inserted thereto (e.g., without limitation, menstrual fluids), or it can be another fluid delivered into the system or included in the system. Prior to use, the dry compounds are included in the system separately from the liquid activator such that molecular hydrogen is generated only when the liquid activator comes in contact with the dry compounds. When the liquid activator is different from biological fluids from the bodily orifice, the system can be configured such that the liquid activator, along with the $H_2$-generating dry compounds, is delivered from an external source such as a container releasably enclosing the liquid activator.

In some embodiments, an elongate body of the system can be placed into (e.g., at least partially dipped into) a liquid activator that penetrates the elongate body to reach the dry compounds within the elongate body, whereby the system is activated to generate molecular hydrogen. Components for generating the liquid activator or the liquid activator can be part of a kit including the system.

A hydrogen-delivering system in accordance with embodiments of the present disclosure can have various configurations. The system can have removable components, such as, for example, an external source of a liquid activator. The system can be self-contained, or it can require that a hydrogen-containing solution is prepared. The liquid activator can be part of a self-contained system, or it can be prepared separately, and the elongate body is placed therein before being inserted into a subject's bodily orifice.

Figure 1:
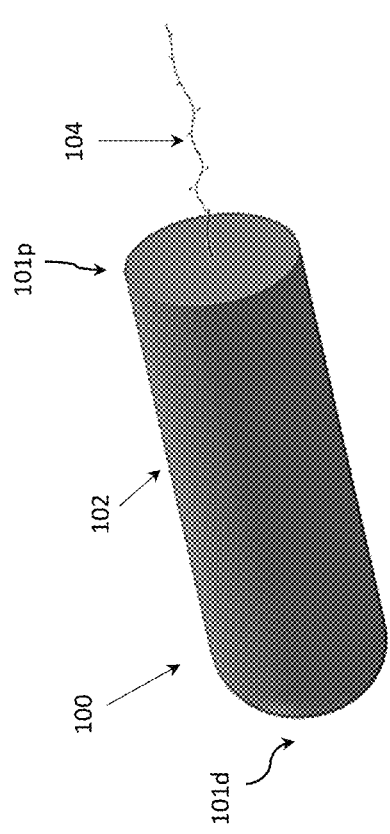
FIG. 1 is a perspective view of a hydrogen-delivering system in accordance with embodiments of the present disclosure, in which an elongate body is configured to be placed into a hydrogen solution.

FIG. 1 shows generally a system 100 in accordance with embodiments of the present disclosure. As shown in FIG. 1, the system 100 includes an elongate body 102 and a pull element 104 extending from a proximal end 101*p* of the elongate body 102. In embodiments, the pull element 104 (e.g., a fabric or plastic string) is low-profile and inconspicuous. In this example, the elongate body 102 is generally cylindrical, though it should be appreciated that the elongate body can have other shapes. The system 100 can be used in embodiments in which a hydrogen solution comprising molecular hydrogen is prepared separately and the elongate body 102, at least an outer layer of which is absorbent, is placed into the hydrogen solution such that at least the outer layer absorbs the solution comprising the molecular hydrogen. In some embodiments, the entire elongate body 102 is absorbent. In embodiments, the hydrogen solution is a hydrogen nanobubbles saturated solution.

In some embodiments, the elongate body 102 is immersed in the hydrogen nanobubbles saturated solution such that the elongate body 102 accumulates molecular hydrogen. In other words, the elongate body 102 absorbs hydrogen nanobubbles and becomes hydrogen-saturated. The elongate body 102 is then inserted (with its distal end 101*d* first) into a bodily orifice of a subject, with at least the outer layer of the elongate body 102 having absorbed the hydrogen solution. The elongate body 102 is allowed to remain seated in the bodily orifice for a time period that allows the molecular hydrogen be released from the elongate body 102 and delivered to tissues in the bodily orifice, to provide therapeutic effect.

After the time period, the pull element 104 is pulled proximally to thereby withdraw the elongate body 102 from the bodily orifice. In this way, the desired therapeutic benefit of the molecular hydrogen is delivered. In some embodiments, the time period is at least 5 minutes, or at least 10 minutes, or at least 15 minutes, or at least 20 minutes, or at least 25 minutes, or at least 30 minutes, or at least 45 minutes, or at least one hour. In some embodiments, the time period is about 5 minutes, or about 10 minutes, or about 15 minutes, or about 20 minutes, or about 25 minutes, or about 30 minutes, or about 45 minutes, or about an hour. In some embodiments, the time period is about 1 hour, or about 2 hours, or about 4 hours, or about 5 hours, or about 6 hours, or about 7 hours, or about 8 hours.

Figure 2B:
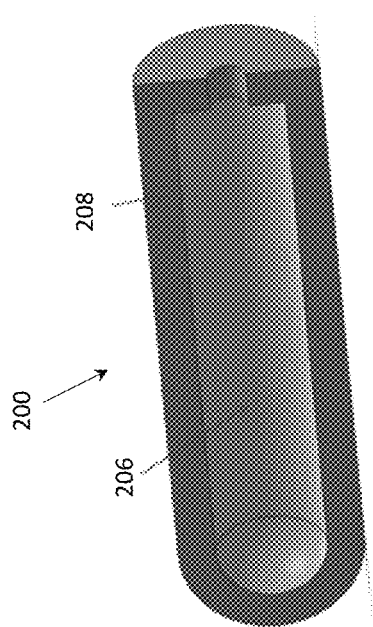
FIG. 2B is a partial, longitudinal cross-sectional view of the elongate body of the hydrogen-delivering system of FIG. 2A.

FIGS. 2A and 2B show another example of a system 200 in accordance with some embodiments of the present disclosure. The system 200 is configured to both absorb biological fluid (e.g., menstrual discharge) and to generate molecular hydrogen. The system 200 is configured to be activated to generate molecular hydrogen using a liquid activator comprising a biological fluid from a subject's bodily orifice, such as, without limitation, the menstrual discharge.

As shown in FIGS. 2A and 2B, the system 200 includes an elongate body 202 having a pull element 204 extending from a proximal end 201p thereof. The pull element 204 can be in the form of a string or another type of element that can be used to remove the elongate body from the bodily orifice. FIGS. 2A an 2B illustrate that the elongate body 202 comprises an inner cavity 206 that can have enclosed therein at least one dry compound (not shown) capable of generating molecular hydrogen upon exposure to a liquid activator. The elongate body 202 also comprises a barrier 208 encompassing the at least one dry compound and that is at least partially hydrogen-permeable and not permeable to the at least one dry compound.

Further, as shown in FIG. 2A, the elongate body 202 comprises an enclosure 210 disposed in the inner cavity 206. The enclosure 210 can be formed by walls of the inner cavity 206, such that there may not be a separate component inserted in the inner cavity 206. In some implementations, however, as discussed in more detail below, the enclosure 210 can be a separate component inserted into the inner cavity 206. The elongate body 202, or a portion thereof (e.g., the enclosure 210) including the dry compounds, in which an $H_2$-generating reaction takes place, can be referred to as a chemical chamber. The enclosure 210 includes the at least one dry compound and, as shown in FIG. 2A, the enclosure 210 can have a plug 203 (or any other type of a closure feature) configured to seal the interior of the enclosure 210. In the example illustrated, the pull element 204 is coupled to the plug 203. It should be appreciated, however, that the pull element 204 can be coupled to the elongate body 202 in other ways. Also, the plug 203 can have various configurations, as it is shown in FIG. 2A by way of example only. In some embodiments, the plug is formed in a cover disposed at the proximal end of the elongate body. For example, the cover can be used to seal the enclosure and/or a proximal end of the elongate body (e.g., elongate body's inner cavity). The cover and the plug can be formed from foam, low durometer molded plastic, or from a similar material.

In the example of FIGS. 2A and 2B, the barrier 208 is in the form of a wall of the elongate body 202. The wall can include two layers—internal (or inner) and external layers (not shown separately), with the external layer disposed concentrically around the inner layer. The internal layer borders the enclosure 210, which can be, e.g., a chemical chamber. The external layer is the outer wall that makes direct contact with the tissues lining the bodily orifice. In this example, both internal and external layers are expandable and at least partially (or entirely) hydrogen-permeable. The layers, or least one of the layers, can expand upon activation of the at least one dry compound upon contact with a liquid activator whereby the molecular hydrogen is generated. The internal layer can be a high capacity absorbent material and is configured to absorb the biological fluids in the bodily orifice, such as, e.g., menstrual discharge. The internal layer can also serve to retain the residue from the chemical compounds used to generate $H_2$, after the $H_2$-generating reaction.

In some implementations, the internal layer can be an outer wall of the enclosure 210. In some embodiments, only one of the internal and external layers can be expandable. For example, the outer layer can expand as it absorbs the bodily fluid, while the inner layer can be not expandable or less expandable than the outer layer (e.g., the inner layer can be formed from a different material). Both the outer and inner layers are permeable to the biological fluid from the bodily orifice such that it can penetrate the layers and reach the dry compound(s) that generate $H_2$ upon exposure to the biological fluid acting as a liquid activator. At least the inner layer is not permeable to the dry compound(s), such that they are safely disposed within the elongate body and do not come in contact with the tissues of the bodily orifice. Both the inner and outer layers are permeable to $H_2$.

FIGS. 3A, 3B, and 3C illustrate generally a system 300 in accordance with some embodiments of the present disclosure in which molecular hydrogen can be generated upon a reaction with a liquid activator delivered to the system 300 from an external source. The system 300 can be a vaginal tampon or anal/rectal suppository (or tampon or applicator). The system 300 includes an elongate body 302, a pull element extending from a proximal end 301p of the elongate body 302, an inner cavity 306 having enclosed therein at least one dry compound capable of generating molecular hydrogen upon exposure to a liquid activator, and a wall 308 encompassing and/or forming the inner cavity. As shown in FIGS. 3A-3B, the system 300 can also include a cover 312 disposed at the proximal end 301p of the elongate body 302, and a plug 314 that seals the inner cavity 306 and/or an enclosure (e.g., a chamber) with the dry compound(s) that can be disposed in the inner cavity 306. The cover 312 is coupled to the elongate body 302 (e.g., welded onto the proximal end of the elongate body 302), or, in some embodiments, the cover 312 forms a part of the elongate body 302.

In some embodiments, the plug 314 includes a diaphragm which closes to seal the inner cavity 306 and/or the enclosure as pressure is exerted on the diaphragm from the generation of molecular hydrogen. In some embodiments, the plug 314 could be nonremovably attached (e.g., glued or otherwise attached) to the cover 312.

The system 300 is activated to generate molecular hydrogen by introducing a liquid activator into the enclosure having the dry compound(s). In some embodiments, the liquid activator used to activate the system 300 is a biological fluid such as, without limitation, menstrual discharge or other biological fluid(s).

In some embodiments, the system 300 can be configured to receive a liquid activator delivered from an external source such as an external container, for example, as described in more detail below in connection with FIGS. 4, 5, 6, and 7. In such embodiments, the system 300 can have components that allow delivering a liquid activator from the external container. Also, for example, the plug 314 of the cover 312, and/or another part of the proximal portion of the elongate body 302, can have openings that allow a liquid activator be provided (e.g., via a tube connector described in more detail below) inside the elongate body 302.

As shown in FIG. 3C, the wall 308 can include internal (or inner) and external (or outer) layers 309i, 309o, which are at least partially permeable to $H_2$. The inner layer 309i borders the enclosure 310, which can be, e.g., a chemical reaction chamber. The outer layer 309o, which may be disposed concentrically around the inner layer 309i, forms an outer wall that makes direct contact with the tissues lining the bodily orifice (e.g., vagina, anus and/or rectum). In some embodiments, the outer layer 309o can be covered with an additional agent, such as a lubricant, moisturizer, etc. In some embodiments, both the inner and outer layers 309i, 309o are expandable and at least partially (or entirely) hydrogen-permeable. One or both of the inner and outer layers 309i, 309o can be formed from an absorbable material. The layers can expand upon activation of the at least one dry compound upon contact with a liquid activator whereby the molecular hydrogen is generated. The inner layer 309i can serve to retain the residue from the chemical compounds used to generate $H_2$, after the $H_2$-generating reaction. Thus, like in other embodiments described herein, the dry compound(s) are safely disposed within the elongate body and do not come in contact with the tissues of the bodily orifice. In some implementations, the inner layer 309i can be an outer wall of an enclosure encompassing the dry compound(s) (not shown).

In some embodiments, only one of the inner and outer layers is expandable. For example, the outer layer can expand as it absorbs the bodily fluid, while the inner layer can be not expandable or less expandable than the outer layer (e.g., the inner layer can be formed from a different material).

In some embodiments, an outer surface of the elongate body is covered with an additional agent, such as, without limitation, a moisturizer, a disinfectant, a lubricant, and/or a therapeutic agent. The additional agent can be a cream, gel, paste, or liquid, and it facilities contact between the outer surface of the elongate body and the tissues of the lining of the bodily orifice. In this way, a likelihood of formation of an empty space between the surface of the elongate body and the tissues of the bodily orifice is reduced or eliminated with the use of an additional agent. The additional agent may facilitate insertion of the elongate body into the bodily orifice. In embodiments, the additional agent does not prevent the diffusion of generated molecular hydrogen into the skin and/or other tissues of the bodily orifice.

FIGS. 4, 5, 6, and 7 further illustrate embodiments of a system which is activated to generate molecular hydrogen by a liquid activator from an external source.

FIG. 4 shows a system 400 for delivery of molecular hydrogen into a bodily orifice of a subject, in accordance with some embodiments of the present disclosure. The system 400 comprises a substantially cylindrical, elongate body 402 having proximal and distal ends 401p, 401d extending between a longitudinal axis A1 thereof, and a pull element extending from the proximal end 401p of the elongate body 402 and configured to be at least partially disposed outside of the bodily orifice when the elongate body 402 is inserted thereto. The elongate body 402, configured to be delivered into the subject's bodily orifice, comprises an inner cavity 406 having enclosed therein at least one dry compound 416 capable of generating molecular hydrogen upon exposure to a liquid activator 420. The dry compound(s) 416, once in contact with the liquid activator, enters a chemical reaction that generates molecular hydrogen.

As shown in FIG. 4, the elongate body 402 comprises a barrier 408 encompassing the at least one dry compound 416 and that is at least partially hydrogen-permeable and not permeable to the at least one dry compound. The barrier 408 can be a wall surrounding the inner cavity 406. Also, an outer wall of the inner cavity 406 can form the barrier 408. In some embodiments, the elongate body 402 comprises an outer layer (which can be absorbent), and an inner layer at least partially encompassing the inner cavity. The inner layer can form the barrier 408.

In embodiments, the barrier 408 is not permeable to the liquid activator such that the liquid activator 420 delivered to the at least one dry compound 416 from the external source is not released to the outside of the elongate body 402.

For purposes of the present disclosure, a "barrier" can be any one or more layers that retain the at least one dry compound within the elongate body and that allow molecular hydrogen generated within the elongate body to be released from within the elongate body and delivered to tissues of the bodily orifice. One or more (or all) layers of the barrier can be absorbent such that they absorb biological fluids in the bodily orifice. In some embodiments, e.g., in which the system is configured for anal/rectal application, only the outer layer of the barrier can be formed from an absorbent material to absorb some of the moisture in the bodily orifice.

In some embodiments, e.g., in which the system is configured for anal/rectal application, the outer layer of the barrier can be formed from a non-absorbent material. A surface of the elongate body can be at least partially covered with a lubricant, moisturizer, or another agent that facilitates insertion of the elongate body into the anus/rectum and facilitates contact between the surface of the elongate body and tissues of the anus and/or rectum.

In the illustrated embodiment, the elongate body 402 comprises a reservoir or enclosure 418 disposed in the inner cavity 406 and including the at least one dry compound 416. In this example, the enclosure 418 is disposed along the longitudinal axis A1 of the elongate body 402. The outer wall of the enclosure 418 can form or can be part of the barrier 408. The outer wall of the enclosure 418 can be made from polyethylene (e.g., in the form of a polyethylene film) or similar hydrogen-permeating material. Also, such material is not permeable to the dry compound(s) 416 and products of the dry compounds' reaction with the liquid activator 420, except that the material is permeable to generated molecular hydrogen.

Figure 6:
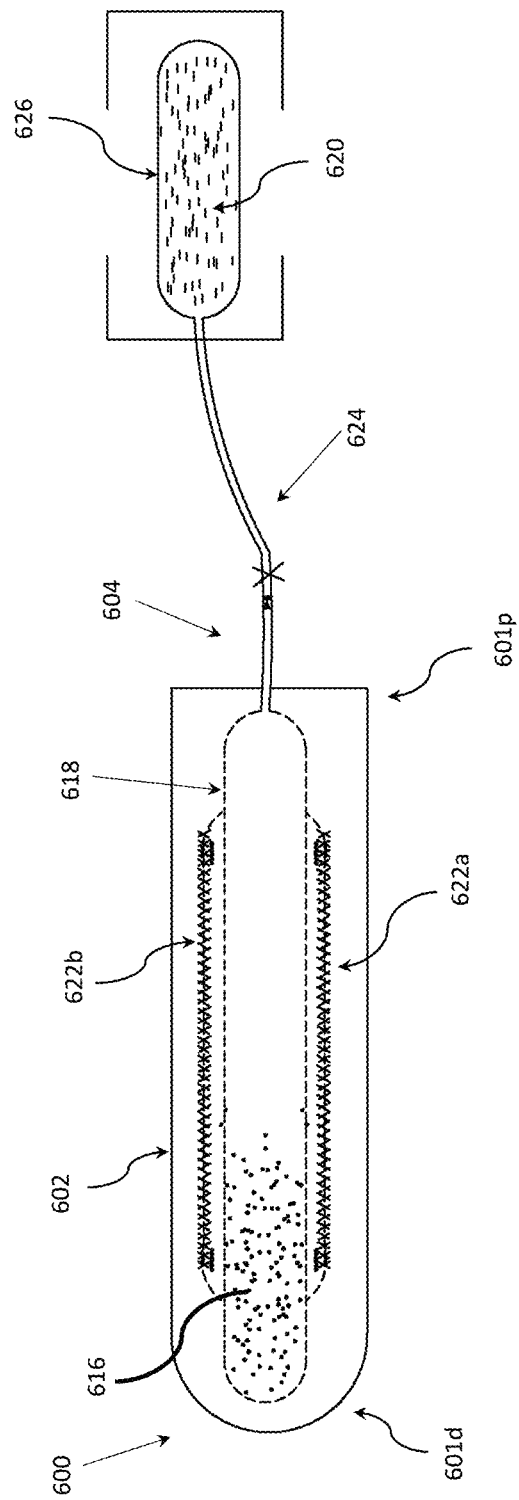
FIG. 6 is a partially transparent, longitudinal cross-sectional view of a hydrogen-delivering system in accordance with embodiments of the present disclosure, wherein an enclosure within the elongate body having at least one dry compound is coupled to the interior of the elongate body at two or more portions of the enclosure.

As shown in FIG. 4, the enclosure 418 can be coupled (422) to the interior of the elongate body 402. For example, the enclosure 418 can be coupled to a wall of the inner cavity 406. In FIG. 4, the enclosure 418 is shown to be coupled to the interior of the elongate body 402 along the enclosure's side, via the coupling feature 422. In some embodiments, as shown in FIG. 6 (discussed below), the enclosure is coupled to the interior of the elongate body along two sides of the enclosure or along two portions of the enclosure. The enclosure 418 can be sewn, welded to, or otherwise anchored to the interior of the elongate body 402. As shown in FIG. 4, the coupling feature 422 extends at least partially along a longitudinal axis of the enclosure 418, wherein the longitudinal axis of the enclosure 418 coincides or substantially coincides with the longitudinal axis A1 of the elongate body 402. It should be appreciated that the coupling feature 422 can additionally or alternatively be formed at least partially around a circumference of the elongate body 402, and/or in other ways.

In some embodiments, the enclosure 418 is integrally formed with at least a portion of the elongate body. In such embodiments, the enclosure 418 is not a separate element from the inner cavity 406, but the walls of the cavity 406 form the enclosure 418. The walls of the inner cavity 406 can be lined with a molecular hydrogen-permeable material that is at the same time not permeable to the dry compound(s) and, in some cases, additionally not permeable to the liquid activator and to the products of the reaction of the dry compounds with the liquid activator.

As shown in FIG. 4, the system 400 comprises a tube connector 424 extending between the elongate body 402 and an activator fluid container 426 such that, in use, the liquid activator 420 releasably disposed in the activator fluid container 426 is delivered to the at least one dry compound 416. The activator fluid container 426 can be included in the system 400, for example, as part of a kit. The activator fluid container 426 is a portable container that is suitable for self-administration of the system.

The activator fluid container 426 releasably stores a bolus of the liquid activator 420 that is sufficient to cause the dry compound(s) to generate $H_2$ as a result of a reaction between the dry compound(s) and the liquid activator 420. In some embodiments, the activator fluid container 426 includes from about 1 ml to about 3 ml, or from about 1.3 ml to about 2.5 ml of a liquid activator. In some embodiments, the activator fluid container 426 includes about 1.1 ml, or about 1.2 ml, about 1.3 ml, or about 1.4 ml, or about 1.5 ml, or about 1.6 ml, or about 1.7 ml, or about 1.8 ml, or about 1.9 ml, or about 2.0 ml, or about 2.1 ml, or about 2.2 ml, or about 2.3 ml, or about 2.4 ml, or about 2.5 ml, or about 2.6 ml, or about 2.7 ml, or about 2.8 ml, or about 2.9 ml, or about 3.0 ml of a liquid activator.

The activator fluid container 426 can be configured to release the liquid activator 420 in various ways. In some embodiments, the activator fluid container 426 can be configured to be moved from a first, initial configuration to a second configuration to thereby release the liquid activator 420 releasably disposed therein. The activator fluid container 426 can be configured to be manipulated to cause the liquid activator 420 be released therefrom and be delivered, via the tube connector 424, to the elongate body 402. The liquid activator 420 can be, without limitation, water, sodium chloride, calcium hydroxide, a buffer (e.g., phosphate buffered saline (PBS), Tris (tris(hydroxymethyl)aminomethane), HEPES (4-(2-hydroxyethyl)-1-piperazineethanesulfonic acid), etc., and variants thereof) or another suitable liquid or similar substance.

In some embodiments, the activator fluid container 426 is configured such that it releases the liquid activator 420 upon pressure applied thereto. FIG. 4 shows schematically that the activator fluid container 426 is associated with a guard element 428 that prevents the activator fluid container 426 from accidental compression and thus prevents premature, inadvertent release of the liquid activator from the activator fluid container 426. The guard element 428 can be any suitable component, such as, e.g., a packaging container that is sufficiently durable to protect the activator fluid container 426 from unintentional compression or other impacts prior to use. The guard element 428 can be made from cardstock, molded plastic, or any other material(s). In some implementations, the activator fluid container 426 can be removably coupled to the guard element 428. In some embodiments, the guard element 428 can be or can be part of a removable package that is removed before use of the system.

In the illustrated embodiment, the tube connector 424 comprises a distal portion 425d that is coupled to the proximal end 401p of the elongate body 402, and a proximal portion 425p coupled to the activator fluid container 426. The distal portion 425d extends between the proximal end 401p of the elongate body 402 to a frangible connection point or portion 430, and the proximal portion 425p extends between the frangible connection portion 430 and a proximal end of the activator fluid container 426. A distal end of the distal portion 425d of the tube connector 424 delivers the liquid activator to the interior of the elongate body 402.

In embodiments, as shown in FIG. 4, the proximal portion 425p of the tube connector 424 is configured to be decoupled from the distal portion 425d of the tube connector 424 after the liquid activator 420 is delivered to the at least one dry compound 426. The proximal portion 425p can be disconnected from the distal portion 425d at the frangible connection portion 430, thereby disconnecting the activator fluid container 426 from the elongate body 402. The frangible connection portion 430 can be configured to be manipulated by a subject to separate the distal and proximal portions 425d, 425p of the tube connector 424 from one another. The tube connector 424 can be cut at its frangible connection portion 430, broken, torn, or otherwise manipulated to remove the proximal portion with the activator fluid container 426 coupled thereto. In some embodiments, the activator fluid container 426 can additionally be separable from the proximal portion of the tube connector 424.

As shown in FIG. 4, the tube connector 424 has a valve 432, such as a non return valve, that allows passage of the liquid activator 420 into the enclosure 418 while preventing backflow of the liquid activator 420. The valve 432, disposed in the distal portion 425d of the tube connector 424, can be made from plastic or other suitable material. In embodiments, the tube connector 424 can be in the form of a low durometer polyethylene tube, or it can be any other element having a passage extended therethrough and formed from any similar material.

In embodiment shown in FIG. 4, the distal portion 425d of the tube connector 424, which remains coupled to the elongate body 402 after the liquid activator is provided to the dry compounds, forms the pull element 404 (e.g., a recovery element) that is used to pull the system 404 after it use out of the bodily orifice. It should be appreciated that the length of the distal portion 425d of the tube connector 424 is sufficient to allow it to be used as the pull element 404. Also, the distal portion 425d of the tube connector 424 is made from a material that allows it to be used as an inconspicuous pull element that remains outside of the bodily orifice while the system 404 is being used to deliver therapeutic properties of molecular hydrogen. a In some embodiments, a system includes both a tube connector coupling an elongate body and an activator fluid container, and a pull element. FIG. 5 illustrates an example of such a system 500 for delivery of molecular hydrogen into a bodily orifice of a subject, in accordance with some embodiments of the present disclosure. The system 500 comprises a substantially cylindrical, elongate body 502, and a pull element extending from a proximal end of the elongate body 502. The elongate body 502 comprises an inner cavity and an enclosure 518 having enclosed therein at least one dry compound 516 capable of generating molecular hydrogen upon exposure to a liquid activator 520.

As shown in FIG. 5, the system 500 includes both the pull element 504 and a tube connector 524 having distal and proximal portions that can be separated from one another at a frangible connection point or portion 530. The tube connector 524 provides a fluidic communication between the activator fluid container 526 and the enclosure 518 having enclosed therein the at least one dry compound 516. The system 500 is similar to system 400 of FIG. 4, and not all components of the system 500 are therefore labeled in FIG. 5 and discussed herein, for the sake of brevity.

As mentioned above, an enclosure, having at least one dry compound, of a system in accordance with embodiments of the present disclosure can be coupled to the interior of an elongate body of the system in more than one portion. FIG. 6 illustrates an example of a system 600 for delivery of molecular hydrogen into a bodily orifice of a subject, in accordance with some embodiments of the present disclosure. The system 600 comprises a substantially cylindrical, elongate body 602 comprising an enclosure 618 having at least one dry compound 616 disposed therein. As shown in FIG. 6, a proximal end 601p of the elongate body 602 is cut at a straight angle (or a substantially straight angle, given manufacturing deviations), while a distal end 601d is curved for comfortable insertion into a bodily orifice.

Like systems 400 and 500 (FIGS. 4 and 5), the system 600 includes an activator fluid container 626 releasably storing the liquid activator 620, and having a tube connector 624 coupled thereto. A distal portion of the tube connector 624 can serve as a pull element 604, or the system 600 can have a separate pull element (not shown). As shown in FIG. 6, the enclosure 618 can be coupled to the interior of the elongate body 602 at two portions via coupling features 622a, 622b, which can be disposed at respective opposite sides of the enclosure 618.

It should be appreciated however that the enclosure 618 can be coupled to the interior of the elongate body 602 in more than two portions, using various features. In some embodiments, the enclosure 618 is coupled to the interior of the elongate body 602 around the entire outer surface of the enclosure 618, or a portion of the outer surface. In addition, in some embodiments, the enclosure is embedded into within the elongate body without the use of any attachment features.

In embodiments, an elongate body of the system, and/or an enclosure having dry compound(s), can have various shapes that facilitate placement of the elongate body into a bodily orifice and allow the elongate body be retained within the bodily orifice until the elongate body is removed from the orifice after use.

In embodiments, the shape of the elongate body changes as the elongate body expands as it absorbs body fluids and/or other fluids. The elongate body can also expand as $H_2$ is generated therein.

In various embodiments, the shape of the elongate body is selected such that the elongate body fits comfortably but snugly within a bodily orifice of a subject. The elongate body can be shaped and sized such that it conforms to the shape of a bodily orifice, such as vagina or anus/rectum. The elongate body can be compressed before the insertion into the bodily orifice, and it can move to an expanded configuration once it is positioned inside the bodily orifice. In some embodiments, the elongate body is partially folded prior to use such that it unfolds during the use. The elongate body can be configured to expand in a manner so that to at least partially abut the walls of the bodily orifice.

Figure 7:
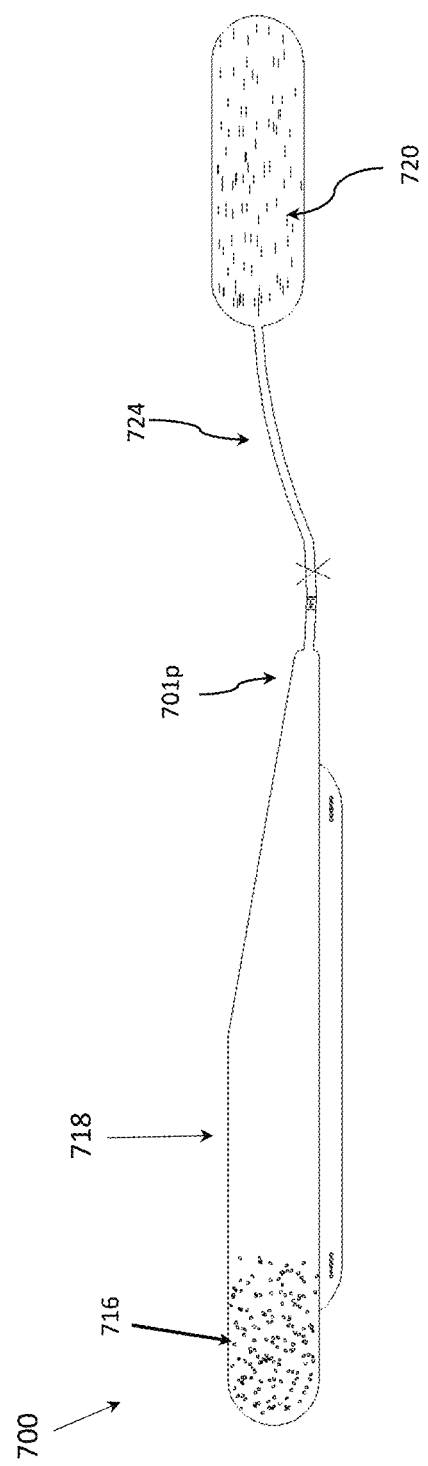
FIG. 7 is a partially transparent, longitudinal cross-sectional view of a hydrogen-delivering system in accordance with embodiments of the present disclosure, wherein an elongate body is proximally tapered.

FIG. 7 illustrates another example of a system 700 in accordance with embodiments of the present disclosure in which a liquid activator 720 is provided to at least one dry compound 716 from an external source via a tube connector 724. In FIG. 7, an enclosure 718 having the at least one dry compound 716 is shown, to illustrate that the enclosure 718 can be proximally tapered such that its circumference decreases towards a proximal end 701p of the enclosure 718. Although an elongate body is not shown in FIG. 700, the elongate body of the system 700 is also proximally tapered in this example. The enclosure 718 can be uniformly tapered towards its proximal end, or the tapering can be slanted.

Figure 8:
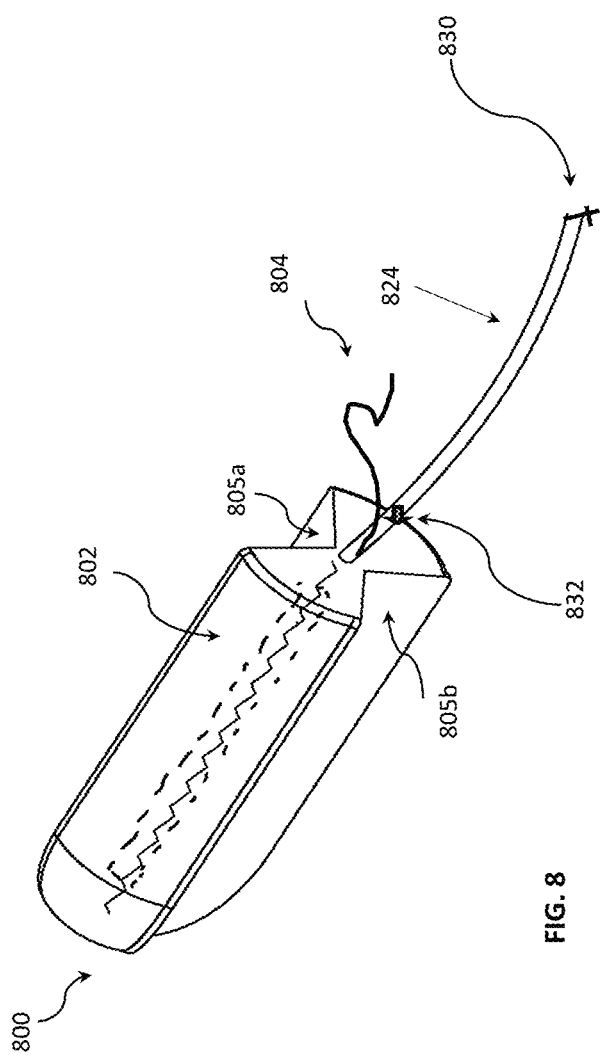
FIG. 8 is a partially transparent, perspective view of another hydrogen-delivering system in accordance with embodiments of the present disclosure, wherein the elongate body is shown after use.

FIG. 8 illustrates another example of a system 800 in accordance with embodiments of the present disclosure in which a liquid activator is provided to at least one dry compound enclosed within an elongate body 802 from an external source via a tube connector 824. In FIG. 8, the system 800 is shown after its use, i.e. after it has been used to deliver molecular hydrogen to the bodily orifice and after it has been withdrawn from the bodily orifice. In use, the elongate body 802 (e.g., at least its outer layer or portion) absorbs fluid(s) from its environment and expands in size (and increases its weight) when saturated. The system 800 comprises a pull element 804 coupled to a proximal end of the elongate body 802, as shown in FIG. 8. The system 800 also comprises a tube connector 824 extending between the elongate body 802 of the system 800 and an activator fluid container (not shown) releasably storing the liquid activator. A distal portion of the tube connector 824, shown in FIG. 8, can be separated from a proximal portion of the tube connector 824 (not shown) after use. As in systems 400, 500, and 600 (FIGS. 4, 5, and 6), the tube connector 824 may include a non return valve 832 (or another similar element), and the distal and proximal portions of the tube connector 824 can be separated from one another at a frangible connection portion 830.

FIG. 8 additionally illustrates that an elongate body of a system in accordance with embodiments of the present disclosure can have a shape that deviates from a cylindrical shape. Thus, as shown in FIG. 8, the elongate body 802 (shown in FIG. 8 after its use) has longitudinal depressions or grooves 805a, 805b at opposite sides thereof. In this example, the The elongate body can additionally or alternatively include other features, such as crevices, ridges, folds, extensions, wings, etc. Any suitable number of features can be formed. The elongate body can be shaped such that it changes its shape and/or size during use.

Figure 9:
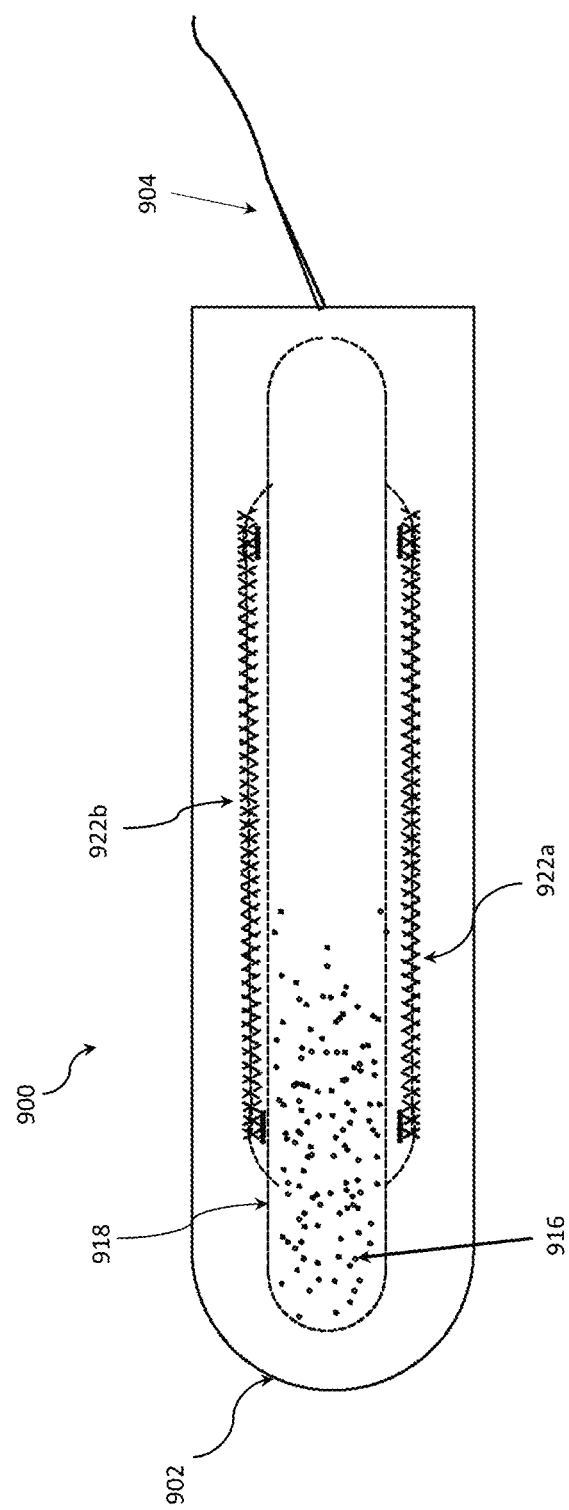
FIG. 9 is a partially transparent, longitudinal cross-sectional view of a hydrogen-delivering system in accordance with embodiments of the present disclosure, wherein an elongate body is configured to receive a liquid activator from a surrounding environment.

In some embodiments, a liquid activator comprises a bodily fluid that is transferred to at least one $H_2$-generating dry compound from a bodily orifice when a system's elongate body is inserted into the bodily orifice. As another variation, an elongate body of the system can be placed into (e.g., at least partially dipped into) the liquid activator that penetrates the elongate body to reach the dry compounds, whereby the system is activated to generate molecular hydrogen. FIG. 9 shows an example of such a system 900 comprising an elongate body 902 having enclosed therein at least one dry compound 916 capable of generating molecular hydrogen upon exposure to a liquid activator, and a pull element 904. The at least one dry compound 916 can be disposed within an enclosure 918 positioned within the elongate body 902 and coupled to the interior of the elongate body 902 at two or more portions of the enclosure 918, using coupling features 922a, 922b. In this example, the coupling features 922a, 922b couple the enclosure 918 at two opposite sides thereof to the elongate body 902, but it should be appreciated that other ways of attaching the enclosure 918 to the interior of the elongate body 902 can be used additionally or alternatively. The enclosure 918 can be sewn, welded, or otherwise anchored to the interior of the elongate body 902.

The elongate body 902 of the system 900 can be dipped into a liquid activator prior to use such that a hydrogen-generating reaction is initiated. The elongate body 902 is then inserted into the bodily orifice where molecular hydrogen is generated and released to the subject's body. The system 900 may be configured for use as an anal applicator or suppository. The system 900 can also be used a vaginal tampon, which can be used when the subject is not menstruating. The elongate body 902, as it generates molecular hydrogen, may absorb small amounts of fluid from its surrounding environment when in use.

Figure 10:
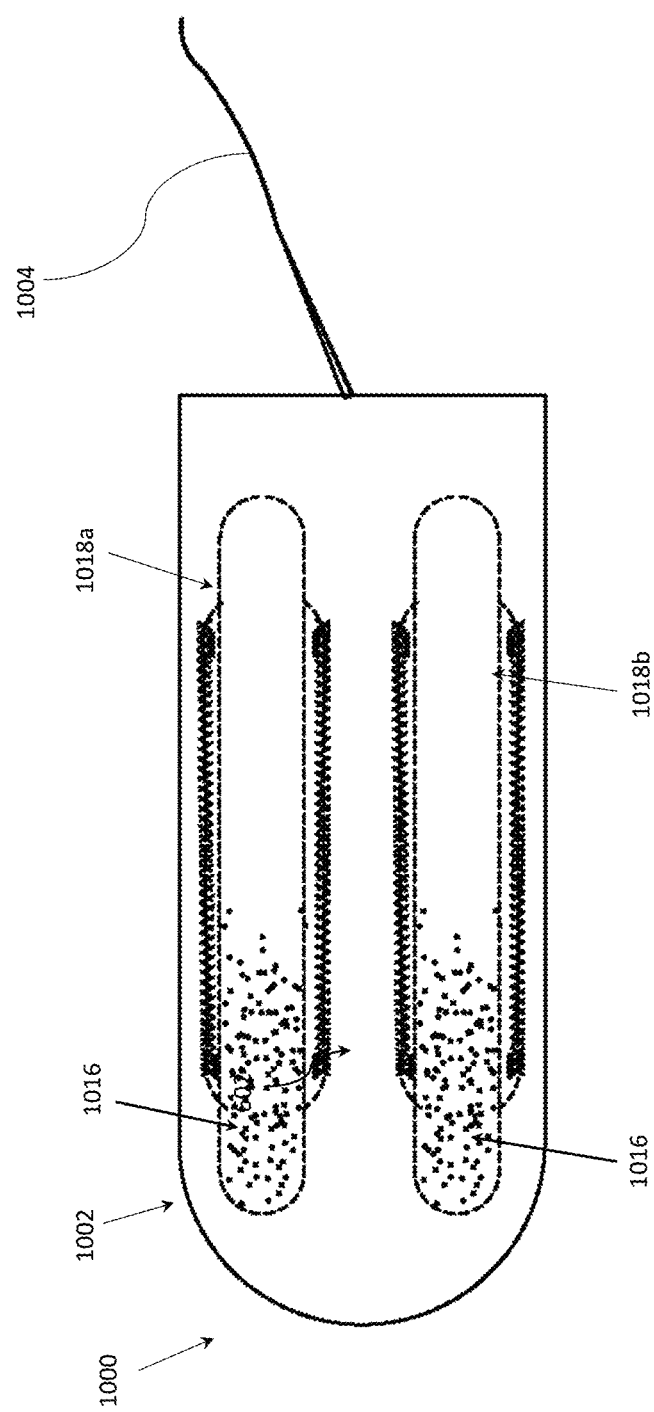
FIG. 10 is a partially transparent, longitudinal cross-sectional view of a hydrogen-delivering system in accordance with embodiments of the present disclosure, wherein an elongate body comprises two enclosures each having enclosed therein at least one dry compound.

FIG. 10 shows a system 1000 which is similar to system 900 of FIG. 9. FIG. 10 however shows the "dual enclosure" system 1000 comprising an elongate body 1002 having first and second enclosures 1018a, 1018b disposed therein, each having at least one dry compounds 1016 stored therein. The system 1000 can be configured to receive a liquid activator from an external source, and the liquid activator can be a biological fluid or another type of fluid.

In embodiments, the first and second enclosures 1018a, 1018b can be disposed in an inner cavity within the elongate body 1002. In this example, each of the first and second enclosures 1018a, 1018b in coupled to the interior of the elongate body 1002 at two opposite sides of the enclosures. It should be appreciated, however, that the enclosures 1018a, 1018b can be coupled to the interior of the elongate body 1002 in various ways, and at one, two, or more portions of the enclosures 1018a, 1018b (and respective portions of the elongate body 1002). In some embodiments, for example, each of the first and second enclosures 1018a, 1018b is coupled to the interior of the elongate body 1002 at first and second sides of the interior (e.g., walls) of the inner cavity, respectively. Furthermore, in some implementations, the first and second enclosures 1018a, 1018b can be inserted into the material forming the elongate body 1002, and the enclosures 1018a, 1018b may not be attached via separate attachment elements to the elongate body 1002.

In FIG. 10, the first and second enclosures 1018a, 1018b are shown to be both disposed along a length of the elongate body 1002. It should be appreciated that the two or more enclosures can alternatively be disposed along a width of the elongate body 1002. Also, the two or more enclosures can have different sizes and shapes from one another, and they can be configured to release molecular hydrogen at different rates.

In some embodiments, a system having more than one enclosure with the dry compound(s) enclosed therein, like system 1000 (FIG. 10) can be used in cases when a release of $H_2$ for a prolonged duration of time is desired. In some embodiments, a size (e.g., a length and/or circumference or the largest dimension) of the two or more enclosures can be smaller than a size of an enclosure in a system having the single enclosure. Also, the two or more enclosures can be configured to release $H_2$ at different rates such that, e.g., $H_2$ is released to the bodily orifice in a staggered manner. In some embodiments, one enclosure releases $H_2$ before another enclosure releases $H_2$. As another variation, an enclosure of the two or more enclosures can release $H_2$ faster than another enclosure of the two or more enclosures. In this way, a time period during which molecular hydrogen is generated by the system is increased.

In some embodiments, a system having more than one enclosure with the dry compound(s) enclosed therein can deliver $H_2$ to body tissues relatively fast, e.g., in less than about 15 minutes, or less than about 10 minutes, or less than about 5 minutes, or less than about 3 minutes, or less than about 1 minute after the delivery of at least a portion of the liquid activator to the enclosure having the dry compound(s). In such embodiments, the two or more enclosures can be disposed closer to the elongate body's surface. Thus, a liquid activator (e.g., a biological fluid) reaches the dry compounds relatively quickly, and the molecular hydrogen is thus generated relatively quickly and is delivered to the walls/tissue of the bodily orifice. One or more enclosures with the dry compound(s) that are disposed farther away from the surface of the elongate body can provide $H_2$ to the outside of the elongate body after the one or more enclosures disposed closer to the elongate body's surface.

In some embodiments, a system having more than one enclosure with the dry compound(s) has enclosures of a smaller size which enclose smaller quantities of dry compounds for activation. Such smaller enclosures require a reduced volume of an activator (e.g., a bodily fluid) for $H_2$ generation and $H_2$ can thus be generated quicker to thereby provide a relatively quick therapeutic effect to tissues of the bodily orifice.

A hydrogen-delivering system in accordance with embodiments of the present disclosure, examples of which are described above, can have variations and modifications.

An enclosure encompassing the at least one dry compound can have a cover at its proximal end. In some embodiments, a plug (made from, e.g., foam, low durometer molded plastic, or another suitable material) can be included in the cover. In some embodiments, the plug allows a tube connector to pass therethrough (e.g., through a bore or channel in the plug) such that a distal end of the tube connector fluidly connects the external source of the liquid activator and the interior of the enclosure.

Regardless of its specific configuration, in some embodiments, a hydrogen-delivering system in accordance with the present disclosure comprises an elongate body and at least a portion of the elongate body is expandable such that, when the elongate body is inserted into the bodily orifice, the elongate body expands to abut tissues in the bodily orifice.

In embodiments, a hydrogen-delivering system is self-contained, easy to use, transport and store, and can be self-administered. The system is configured to be self-administered.

Dry compounds that can be included in a hydrogen-delivering system in accordance with embodiments of the present disclosure can be various biopolymers and nano-materials that can store a significant amount of hydrogen. Some of these materials release hydrogen when aqueous solutions are applied. The dry compounds can be selected based on known hydrogen-releasing chemical reactions (e.g., the reactions of the electrochemical series of elements (Ca, Mg, Al, Zn, Fe) with water, acids or bases). In some embodiments, the dry compounds comprise Si, e.g., Si nanopowder. See Kobayashi et al., *J Nanopart Res* (2017) 19: 176, which is incorporated by reference herein in its entirety. The dry compounds are selected for inclusion in a hydrogen-delivering system based on their safety, ecological compatibility, stability to long-term storage, and other factors.

The chemical compounds are selected such that they react in a safe way, without generating excess of hydrogen (which may be flammable in extreme circumstances). Also, when more than one dry compound is used, the compounds do not react until they come in contact with a liquid activator such as a biological fluid, an aqueous composition, or another activator liquid. Non-limiting examples of the non-biological liquid activator include a water suspension of calcium hydroxide, a water solution of sodium chloride and copper (II) sulfate, water, a suitable acid, base, and other suitable solutions. Non-limiting examples of the dry compounds include electrochemical series, e.g., aluminum, magnesium, zinc, iron; and compounds such as, e.g., magnesium hydride, calcium hydride, biopolymers and other suitable dry compounds where hydrogen is stored and is released once in contact with a liquid (e.g., water or another liquid) solution, or their mixture(s). Molecular hydrogen can be produced from a suitable chemical reaction, or it can be released from molecular storage. Components used to produce hydrogen are safe and, in some embodiments, are Generally Recognized As Safe (GRAS)-certified.

In some embodiments, a hydrogen-delivering system (e.g., an elongate body thereof) has metallic aluminum (e.g., foil, powder, or another form) that is covered by aluminum oxide. A liquid activator, such as a water suspension of food-grade calcium hydroxide, $Ca(OH)_2$ ("slaked lime"), when in contact with the metallic aluminum covered by aluminum oxide, activates the following set of chemical reactions to generate $H_2$:

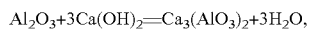
$Al_2O_3 + 3Ca(OH)_2 = Ca_3(AlO_3)_2 + 3H_2O$,

$2Al + 6H_2O = 2Al(OH)_3 + 3H_2\uparrow$,

$2Al + 3Ca(OH)_2 = Ca_3(AlO_3)_2 + 3H_2\uparrow$, and

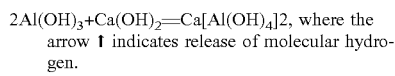
$2Al(OH)_3 + Ca(OH)_2 = Ca[Al(OH)_4]2$, where the arrow ↑ indicates release of molecular hydrogen.

In some embodiments, a hydrogen-delivering system (e.g., an elongate body thereof) includes a metallic magnesium (e.g., flakes or powder) that is covered by magnesium oxide. A liquid activator, such as, e.g., a water suspension of citric acid, when in contact with the metallic magnesium covered by magnesium oxide, activates the following reaction to generate $H_2$;

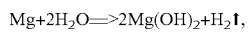
$Mg + 2H_2O =\!> 2Mg(OH)_2 + H_2\uparrow$, where the arrow ↑ indicates release of molecular hydrogen.

The hydrogen-delivering system in accordance with embodiments of the present disclosure can be administered to a bodily orifice for treatment of various conditions and disorders. For example, in some embodiments, the system can be administered to a subject that has a disease, disorder, or condition of a vaginal area or anal/rectal area. The system can thus be used in a method of treatment of a subject in need thereof, wherein the method causes a treatment and/or mitigation of the disease, disorder, or condition of the vagina or anal/rectal area.

In some embodiments, a method for alleviating or preventing dysmenorrhea is provided, including for alleviating, preventing, or treating cramps, abdominal and (lower) back pain, diarrhea, headache, nausea, and other symptoms of dysmenorrhea. In embodiments, dysmenorrhea is defined as a combination of least of abdominal pain, negative affect/somatic complaints, and back pain. See Negriff et al., *J Health Psychol.* 2009; 14(7):899-908.

In some embodiments, a method for alleviating or preventing premenstrual syndrome (PMS) is provided, including for alleviating, preventing, or treating breast tenderness, abdominal bloating, headache, and swelling of extremities, and other symptoms of PMS.

The system can also be used to treat a wound in the vaginal area or anal/rectal area.

In some embodiments, a method for treating anal fissures or another anal disorders is provided.

In some embodiments, a method for alleviating pain in a bodily orifice is provided. Molecular hydrogen can have antispasmodic effect.

In some embodiments, the described methods and systems can be used for alleviating menopause symptoms, including, without limitation, vaginal dryness.

Because molecular hydrogen does not have known contradictions, the described methods and systems can be safety used by subjects regardless of subjects' underlying conditions. Also, the described methods can be used in combination with any therapies or medications.

As discussed above, a hydrogen-delivering system in accordance with embodiments of the present disclosure can have various configurations. For example, in some embodiments, the system can resemble a conventional vaginal tampon, though it has features that make it different from existing tampons.

A hydrogen-delivering system in accordance with embodiments of the present disclosure can be configured to generate from about 0.1 mmol to about 5 mmol, or from about 0.5 mmol to about 5 mmol, or from about 0.5 mmol to about 2.5 mmol, or from about 0.5 mmol to about 1.5 mmol, or from about 0.3 mmol to about 1 mmol, or about 1 mmol of $H_2$. In some embodiments, the system is configured to generate about 1 mmol of $H_2$ that is sufficient to effectively deliver the therapeutic agent to the subject's body.

In embodiments, molecular hydrogen is delivered to tissues in the bodily orifice for a certain period of time, selected to be sufficient to provide a desired therapeutic effect. The period of time can be, for example, from about 1 minute to about two hours, or from about 1 minute to about one hour, or from about 1 minute to about 30 minutes, or from about 1 minute to about 20 minutes, or from about 1 minute to about 10 minutes, or from about 10 minutes to about 30 minutes. In some embodiments, the period of time can be from about 30 minutes to about 2 hours. In some embodiments, the period of time can be from about 1 hour to about 8 hours, or from about 1 hour to about 6 hours, or from about 1 hour to about 8 hours, or from about 2 hours to about 4 hours, or from about 2 hours to about 8 hours, or from about 4 hours to about 8 hours, or from about 2 hours to about 6 hours.

The hydrogen-delivering system can be configured to release hydrogen for a predetermined duration of time. In the course of therapy, multiple hydrogen-enhanced system in accordance with embodiments of the present disclosure can be applied to a target tissue (which can be intact or wounded skin area) of the bodily orifice. For example, the therapy can involve application of hydrogen-delivering systems of the same or different type(s) to the bodily orifice over a period of a day, several days, a week, several weeks, or over any other period of time.

In some embodiments, a therapy which makes use of a system and method of use thereof in in accordance with embodiments of the present disclosure is delivered in a regimen that comprises one day, or 2 days, or 3 days, or 4 days, or 5 days, or 6 days, or about one week, or about 2 weeks, or about 3 weeks, or about 4 weeks, or for a longer period of time. The therapy can be administered once a day, or two times a day, or 3 times a day, or 4 times a day. In some embodiments, the system can be administered once, to achieve a desired effect. In embodiments, the system is used as need, for example, upon onset of PMS symptoms or upon onset of dysmenorrhea symptoms. In embodiments, the system is used for treatment and prevention of various other conditions, including wounds.

DEFINITIONS

The following definitions are used in connection with the invention disclosed herein. Unless defined otherwise, all technical and scientific terms used herein have the same meaning as commonly understood to one of skill in the art to which this invention belongs.

Further, the term "about" when used in connection with a referenced numeric indication means the referenced numeric indication plus or minus up to 10% of that referenced numeric indication. For example, the language "about 50" covers the range of 45 to 55.

As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the present invention, the present disclosure, or embodiments thereof, may alternatively be described using alternative terms such as "consisting of" or "consisting essentially of."

Since other modifications and changes varied to fit particular operating requirements and environments will be apparent to those skilled in the art, the present disclosure is not considered limited to the examples chosen for purposes of disclosure, and covers all changes and modifications which do not constitute departures from various embodiments, or combinations of the embodiments, of the present disclosure.

EQUIVALENTS

While the present disclosure has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

INCORPORATION BY REFERENCE

Those skilled in the art will recognize, or be able to ascertain, using no more than routine experimentation, numerous equivalents to the specific embodiments described specifically herein. Such equivalents are intended to be encompassed in the scope of the following claims.

All patents and publications referenced herein are hereby incorporated by reference in their entireties.

The publications discussed herein are provided solely for their disclosure prior to the filing date of the present application. Nothing herein is to be construed as an admission that the present invention is not patentable in view of such publications.

As used herein, all headings are simply for organization and are not intended to limit the disclosure in any manner. The content of any individual section may be equally applicable to all sections.

What is claimed is:

1. A system for delivery of molecular hydrogen into a bodily orifice of a subject, the system comprising:
    a cylindrical, elongate body having proximal and distal ends extending between a longitudinal axis thereof, and configured to be delivered into the bodily orifice, wherein the elongate body comprises:
        an inner cavity having enclosed therein at least one dry compound capable of generating molecular hydrogen upon exposure to a liquid activator; and
        a barrier encompassing the at least one dry compound and that is at least partially hydrogen-permeable and not permeable to the at least one dry compound;
    wherein the elongate body comprises an absorbent layer at least partially encompassing the inner cavity that has the at least one dry compound; and
    a pull element extending from the proximal end of the elongate body and configured to be at least partially disposed outside of the bodily orifice when the elongate body is inserted into the bodily orifice.

2. The system of claim 1, wherein the liquid activator comprises a bodily fluid that is transferred to the inner cavity through the barrier when the elongate body is inserted into the bodily orifice.

3. The system of claim 1, wherein the elongate body comprises an outer absorbent layer, and an inner layer at least partially encompassing the inner cavity, wherein the inner layer comprises the barrier, and wherein the outer absorbent layer absorbs and retains the bodily fluid when the elongate body is inserted into the bodily orifice.

4. The system of claim 1, wherein the liquid activator is delivered to the at least one dry compound from an external source.

5. The system of claim 4, wherein the barrier is not permeable to the liquid activator such that the liquid activator delivered to the at least one dry compound from the external source is not released to the outside of the elongate body.

6. The system of claim 1, further comprising a cover disposed at the proximal end of the elongate body.

7. The system of claim 6, wherein the cover has the pull element coupled thereto, wherein the pull element optionally comprises a string.

8. The system of claim 1, comprising an enclosure disposed in the inner cavity including the at least one dry compound, wherein the enclosure is optionally coupled to an interior of the elongate body or is integrally formed with at least a portion of the elongate body.

9. The system of claim 1, having a tube connector extending between the elongate body and an activator fluid container such that the liquid activator releasably disposed in the activator fluid container is delivered to the at least one dry compound.

10. The system of claim 9, further comprising the activator fluid container removably coupled to the elongate body via the tube connector, wherein the activator fluid container is configured to be moved from a first, initial configuration to a second configuration to thereby release the liquid activator releasably disposed therein.

11. The system of claim 9, wherein the tube connector comprises a distal portion that is coupled to the proximal end of the elongate body, and a proximal portion coupled to the activator fluid container, and wherein the proximal portion of the tube connector is configured to be decoupled from the distal portion of the tube connector after the liquid activator releasably disposed in the activator fluid container is delivered to the at least one dry compound, thereby disconnecting the activator fluid container from the elongate body.

12. The system of claim 9, wherein the tube connector comprises a valve.

13. The system of claim 11, wherein the pull element comprises the distal portion of the tube connector.

14. The system of claim 9, wherein the pull element is separate from the tube connector.

15. The system of claim 1, wherein the barrier is formed by an inner wall of the elongate body forming the inner cavity.

16. The system of claim 1, wherein the elongate body is in the form of a tampon configured to be inserted into the bodily orifice comprising a vagina.

17. The system of claim 16, wherein the liquid activator comprises menstrual blood and/or bodily fluids from the vagina.

18. The system of claim 1, wherein the elongate body is in the form of an anal suppository configured to be inserted into the bodily orifice comprising an anal canal and/or rectum.

19. The system of claim 1, wherein at least a portion of the elongate body is expandable such that, when the elongate body is inserted into the bodily orifice, the elongate body expands to abut tissues in the bodily orifice.

20. A method of delivering molecular hydrogen to tissues in a bodily orifice of a subject, the method comprising:
- inserting into the bodily orifice an elongate body configured to generate molecular hydrogen, wherein the elongate body has enclosed in an inner cavity thereof at least one dry compound capable of generating molecular hydrogen upon exposure to a liquid activator, a barrier encompassing the at least one dry compound and that is at least partially hydrogen-permeable and not permeable to the at least one dry compound, wherein the elongate body comprises an absorbent layer at least partially encompassing the inner cavity that has the at least one dry compound, and wherein the elongate body has a pull element coupled to a proximal end thereof;
- allowing the at least one dry compound included in the elongate body generate the molecular hydrogen upon exposure to the liquid activator to thereby deliver the molecular hydrogen to tissues in the bodily orifice; and
- after a time period, pulling the pull element proximally to thereby withdraw the elongate body from the bodily orifice after the molecular hydrogen is delivered to the tissues in the bodily orifice.

\* \* \* \* \*